United States Patent [19]
Kung et al.

[11] Patent Number: 6,156,758
[45] Date of Patent: Dec. 5, 2000

[54] ANTIBACTERIAL QUINAZOLINE COMPOUNDS

[75] Inventors: Pei-Pei Kung, Leucadia; Phillip Dan Cook, Fallbrook; Charles John Guinosso, Vista, all of Calif.

[73] Assignee: Isis Pharmaceuticals, Inc., Carlsbad, Calif.

[21] Appl. No.: 09/391,843

[22] Filed: Sep. 8, 1999

[51] Int. Cl.$^7$ .................... A61K 31/517; A61K 31/395; C07D 239/72

[52] U.S. Cl. .................... 514/260; 514/252.14; 544/283; 544/292

[58] Field of Search ............... 514/260, 292.14; 544/284, 292, 283

[56] References Cited

FOREIGN PATENT DOCUMENTS

| | | |
|---|---|---|
| WO 93/04048 | 3/1993 | WIPO. |
| 9512584 | 5/1995 | WIPO. |
| 9512592 | 5/1995 | WIPO. |
| 9723216 | 7/1997 | WIPO. |

OTHER PUBLICATIONS

Gazit et al., "Tyrphostins IV—Highly Potent Inhibitors of EGF Receptor Kinase. Structure—Activity Relationship Study of 4–Anilidoquinazolines," *Bioorg. Med. Chem.*, 1996, 4(8), 1203–1207.

Kukla et al., "Synthesis and Anti–HIV–1 Activity of 4,5,6,7,–Tetrahydro–5–methylimidazo[4,5,1–jk][1,4]benzodiazepin–2(1H)–one (TIBO) Derivatives," *J. Med. Chem.*, 1991, 34, 746–715.

Mach et al., "$^{18}$F–Labeled Benzamides for Studying the Dopamine $D_2$ Receptor with Positron Emission Tomography," *J. Med. Chem.*, 1993, 36, 3707–3720.

Marchbanks, C. et al., "New Fluoroquinolones", *Hospital Therapy*, 1988, 7, 18–19, 23–27, 31, and 34–35.

Miyamoto et al., "Pyridonecarboxylic Acids as Antibacterial Agents. VIII. An Alternative Synthesis of Enoxacin via Fluoronicotinic Acid Derivatives," *Chem. Pharm. Bull.*, 1987, 35, 2280–2285.

Parry, M., "Pharmacology and Clinical Uses of Quinolone Antibiotics", *Medical Times*, 1988, 116(12), 39–45 and 19.

Shah, P., "Quinolones", *Prog. Drug Res.*, 1987, 31, 243–256.

Wagaw et al., "The Synthesis o Aminopyridines: A Method Employing Palladium–Catalyzed Carbon–Nitrogen Bond Formation," *J. Org. Chem.*, 1996, 61, 7240–7241.

Wolfe et al, "An Improved Catalyst System for Aromatic Carbon–Nitrogen Bond Formation: The Possible Involvement of Bis(Phosphine) Palladium Complexes as Key Intermediates," *J. Am. Chem. Soc.*, 1996, 118, 7215–7216.

*Primary Examiner*—Mukund J. Shah
*Assistant Examiner*—Sudhaker B. Patel
*Attorney, Agent, or Firm*—Woodcock Washburn Kurtz Mackiewicz & Norris LLP

[57] ABSTRACT

Provided are compounds of formula (I)

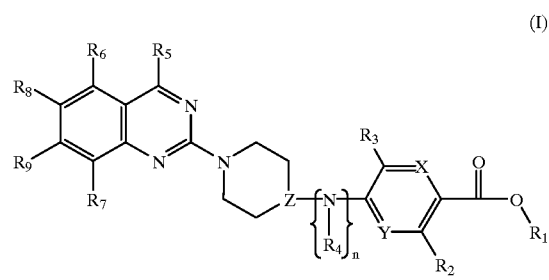

wherein X, Y and Z are independently CH or N; n is 0 or 1; $R_1$ is selected from OH, alkoxy, aryloxy, aralkyloxy and guanidinyl; $R_2$ and $R_3$ are independently selected from H, halogen, amino, hydroxyl, nitro, cyano and carboxyl; $R_4$ is H, alkyl or acyl; $R_5$ is selected from H, hydroxyl, halogen, nitro, alkyl, alkoxy, amino, cyclic amino, alkylamino, arylamino and aralkylamino wherein the alkyl, aryl and cyclic moieties are optionally substituted; $R_6$ and $R_7$ are independently selected from H, alkyl, alkoxy, halogen and amino; and $R_8$ and $R_9$ are independently selected from H, $C_{1-4}$ alkyl, alkoxy, acyl, acyloxy, alkoxycarbonyl, hydroxyl, halogen, amino and carboxyl. The compounds have therapeutic or prophylactic use for treating bacterial infection in mammals.

17 Claims, 3 Drawing Sheets

ANTIBACTERIAL QUINAZOLINE COMPOUNDS

FIELD OF THE INVENTION

The present invention relates to novel compounds useful as therapeutic agents, in particular quinazoline compounds that have antimicrobial activity.

BACKGROUND OF THE INVENTION

The chemical and medical literature describes a myriad of compounds that are said to be antimicrobial, i.e., capable of destroying or suppressing the growth or reproduction of microorganisms, such as bacteria. In particular, antibacterials include a large variety of naturally-occurring (antibiotic), synthetic, or semi-synthetic compounds. They may be classified as aminoglycosides, ansamacrolides, beta-lactams (including penicillins and cephalosporins), lincosaminides, macrolides, nitrofurans, nucleosides, oligosaccharides, peptides and polypeptides, phenazines, polyenes, polyethers, quinolones, tetracyclines, and sulfonamides. Such antibacterials and other antimicrobials are described in Antibiotics, Chemotherapeutics, and Antibacterial Agents for Disease Control (M. Grayson, editor, 1982), and E. Gale et al., The Molecular Basis of Antibiotic Action 2d edition (1981).

The mechanism of action of these antibacterials vary. However, each can be generally classified as functioning in one or more of four ways: by inhibiting cell wall synthesis or repair; by altering cell wall permeability; by inhibiting protein synthesis; or by inhibiting synthesis of nucleic acids. For example, beta-lactam antibacterials act through inhibiting the essential penicillin binding proteins (PBPs) in bacteria, which are responsible for cell wall synthesis. On the other hand, quinolones act by inhibiting synthesis of bacterial DNA, thus preventing the bacteria from replicating.

Not surprisingly, the pharmacological characteristics of antibacterials and other antimicrobials, and their suitability for any given clinical use also vary considerably. For example, the classes of antimicrobials (and members within a class) may vary in their relative efficacy against different types of microorganisms, and their susceptibility to development of microbial resistance. These antimicrobials may also differ in their pharmacological characteristics, such as their bioavailability, and biodistribution. Accordingly, selection of an appropriate antibacterial (or other antimicrobial) in any given clinical situation can be a complicated analysis of many factors, including the type of organism involved, the desired method of administration, and the location of the infection to be treated.

The pharmaceutical literature is replete with attempts to develop improved antimicrobials (i.e., compounds that have a broader scope of activity, greater potency, improved pharmacology, and/or less susceptibility to resistance development.) For example, one group of antimicrobials that has been developed relatively recently for clinical use is the quinolones. These compounds include, for example, nalidixic acid, difloxacin, enoxacin, fleroxacin, norfloxacin, lomefloxacin, ofloxacin, ciprofloxacin, and pefloxacin.

See, C. Marchbanks and M. Dudley, "New Fluoroquinolones", 7 Hospital Therapy 18 (1988); P. Shah, "Quinolones", 31 Prog. Drug Res. 243 (1987); Quinolones—Their Future in Clinical Practice, (A. Percival, editor, Royal Society of Medical Services, 1986); and M. Parry, "Pharmacology and Clinical Uses of Quinolone Antibiotics", 116 Medical Times 39 (1988).

However, many such attempts to produce improved antimicrobials have produced equivocal results. For example, the quinolones often show reduced effectiveness against certain clinically important pathogens (for example, gram positive bacteria and/or anaerobic bacteria). The quinolones also have limited water solubility limiting their bioavailability and suitability for parenteral dosing. They may also produce adverse side effects, such as gastrointestinal disturbance and central nervous system effects such as convulsions. Accordingly there remains a need for new effective antimicrobial compounds.

SUMMARY OF THE INVENTION

According to an aspect of the present invention there is provided compounds of formula (I)

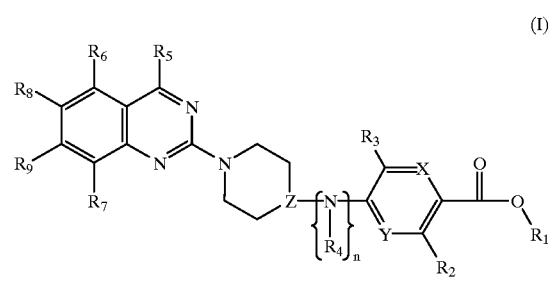

(I)

wherein

X, Y and Z are independently CH or N;

n is 0 or 1;

$R_1$ is selected from OH, alkoxy, aryloxy, aralkoxy and guanidinyl;

$R_2$ and $R_3$ are independently selected from H, halogen, amino, hydroxyl, nitro, cyano and carboxyl;

$R_4$ is H, alkyl or acyl;

$R_5$ is selected from H, hydroxyl, halogen, nitro, alkyl, alkoxy, amino, cyclic amino, alkylamino, arylamino and aralkylamino wherein the alkyl, aryl and cyclic moieties are optionally substituted;

$R_6$ and $R_7$ are independently selected from H, alkyl, alkoxy, halogen and amino; and $R_8$ and $R_9$ are independently selected from H, alkyl, alkoxy, acyl, acyloxy, alkoxycarbonyl, hydroxyl, halogen, amino and carboxyl.

In another aspect of the invention there is provided a method of treating bacterial infection in a mammal comprising administering to said mammal an effective amount of a quinazoline compound of the invention.

DETAILED DESCRIPTION OF THE INVENTION

Figure 1:
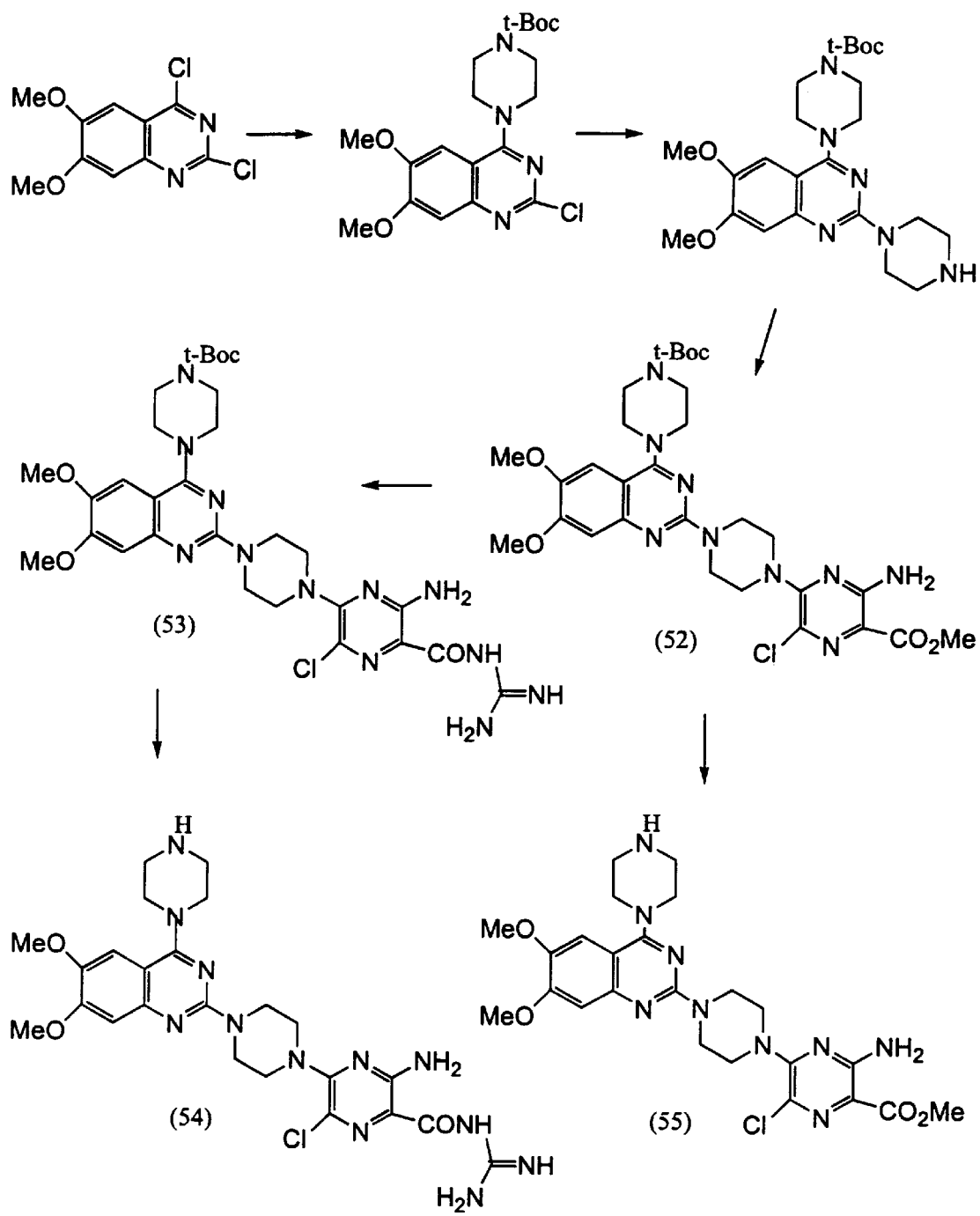
FIG. 1 is a schematic representation of a synthetic route for preparing compounds described in examples 33, 34 and 35.

Quinazoline compounds are provided having therapeutic activity, in particular antibacterial activity having the general formula (I)

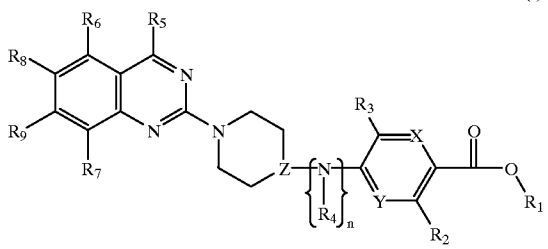

(I)

wherein

X, Y, Z, n and $R_1$ to $R_9$ are as previously defined.

In a particular embodiment, n is 1 and Z is CH. In an alternative embodiment n is 0 and Z is N provided that when $R_2$ and $R_5$ are both $NH_2$, $R_3$ is Cl, $R_6$ and $R_7$ are both H and $R_8$ and $R_9$ are both OMe, Z is N and n is 0 then $R_1$ is other than guanidinyl.

In a preferred embodiment X is CH while Y is CH or N. In a particularly preferred embodiment X and Y are both CH. Alternatively X and Y are both N.

$R_1$ is selected from OH, alkoxy, aryloxy, aralkyloxy and guanidinyl (—NH—C(NH)—$NH_2$). By "alkoxy" is meant herein to be a carbon chain depending from an oxygen atom (i.e. —O—alkyl), wherein the carbon chain is branched or unbranched, saturated or unsaturated (i.e. including alkenyloxy and alkynyloxy). Preferred alkyl chains have from 1 to 8 carbons and more preferably 1 to 4 carbons. Particularly preferred alkoxy groups include OMe, OEt, O—nPr, O—iPr, O—nBu, O—iBu, O—sBu and O—tBu. In a particularly preferred embodiment $R_1$ is OH. By "aryloxy" is meant herein to be a substituted or unsubstituted carbocyclic or heterocyclic ring or ring system of 5 to 12 members depending from an oxygen atom. Substituents on the aryl moiety includes OH, amino, halogen and alkyl. The ring or ring system includes those that are partially or entirely unsaturated as well as aromatic ring or ring systems. Preferred aryloxy groups include phenoxy, O-naphthyl, O-pyridyl, O-piperidinyl, O-imidazolyl, O-indolyl and O-pyrrolyl.

$R_2$ and $R_3$ are independently selected from H, halogen, amino, hydroxyl, nitro, cyano and carboxyl. By "amino" is meant herein to be a primary ($NH_2$), secondary (—NHR) or tertiary amine (—NRR). Substituents on secondary and tertiary amines include alkyl, aralkyl and aryl (as previously defined). In preferred embodiments $R_2$ and $R_3$ are independently $NH_2$ or Cl. By "carboxyl" is meant herein to include —COOH as well as esters thereof, in particular alkyl esters such as Me, Et and tBu.

$R_4$ is H, alkyl or acyl. By "acyl" is meant herein to be a substituent having a carbonyl function adjacent to group from which the substituent is attached. Preferred acyl groups include alkyl carbonyl, aryl carbonyl and aralkyl carbonyl wherein alkyl, aryl and aralkyl are as previously defined. In a preferred embodiment $R_4$ is $C_{1-4}$ alkyl such as methyl. In a particularly preferred mbodiment $R_4$ is H.

$R_5$ is selected from H, hydroxyl, halogen, nitro, alkyl, alkoxy, amino, cyclic amino, alkylamino, arylamino and aralkylamino wherein the alkyl, aryl and cyclic moieties are optionally substituted. Preferred substituents are alkyl(i.e. $C_{1-4}$ alkyl), OH, amino, and halogen. By "alkyl" is meant a chain of preferably 1 to 8 carbon atoms, straight or branched and saturated or unsaturated i.e. including alkenyl and alkynyl. In a preferred embodiment $R_5$ is amino, cyclic amino, alkylamino, arylamino or aralkylamino optionally substituted. In a particularly preferred embodiment $R_5$ is optionally substituted arylamino. The aryl moiety may be mono, bi or tricyclic and includes heteroaryl. A preferred arylamino group is optionally substituted phenylamino i.e. —NH—(4-methylphenyl) (4 mpa). In another preferred embodiment $R_5$ is amino which includes $NH_2$ as well as protected amino i.e. —NH—tBoc. In another preferred embodiment $R_5$ is cyclic amino i.e. a tertiary amine, the nitrogen atom of the amine incorporated in a saturated or unsaturated ring or ring system which optionally incorporates other heteroatoms (N, S or O). Preferred cyclic amino groups include morpholine, piperidine and piperazine. Piperazine includes N4 protected piperazine i.e. tBoc piperazine or N4 substituted piperazine i.e. alkylpiperazine.

$R_6$ and $R_7$ are independently selected from H, alkyl, alkoxy, halogen and amino. Preferred alkyl and alkoxy groups are $C_{1-4}$ and more preferably methyl and methoxy respectively. Preferred halogen is Cl. In a particularly preferred embodiment both $R_6$ and $R_7$ are H.

$R_8$ and $R_9$ are independently selected from H, alkyl, alkoxy, acyl, acyloxy, alkoxycarbonyl, hydroxyl, halogen, amino and carboxyl. By "acyloxy" and "alkoxycarbonyl" are meant herein to be substituents having a —O—C(O)—R and —C(O)—O—R functionality respectively adjacent to the group from which they depend. The R portion of the acyloxy is preferably alkyl, aryl or aralkyl (as previously defined). In a particular embodiment $R_8$ and $R_9$ are both alkoxy, preferably $C_{1-4}$ alkoxy. In a particularly preferred embodiment $R_8$ and $R_9$ are both methoxy.

Preferred compounds of the invention include:

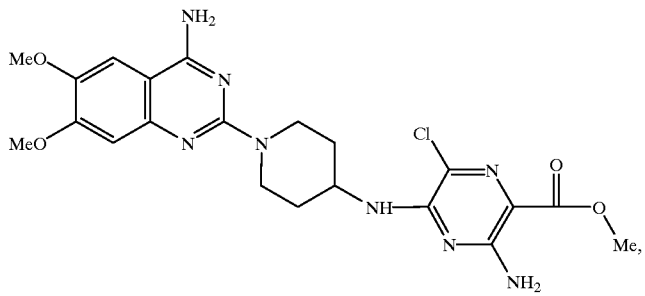

-continued

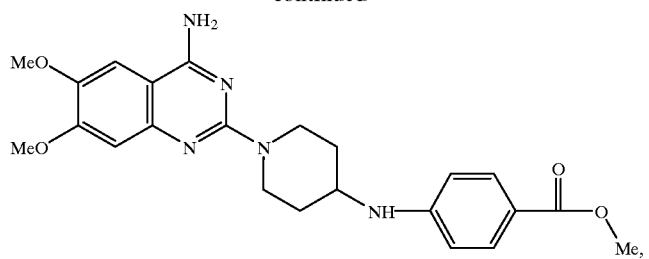

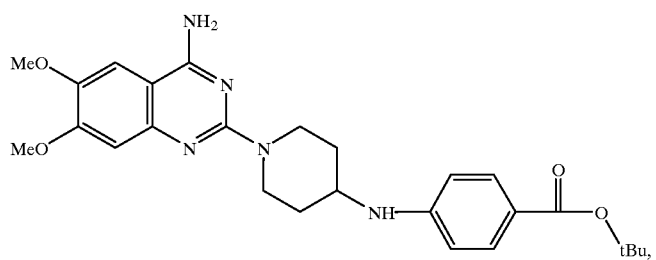

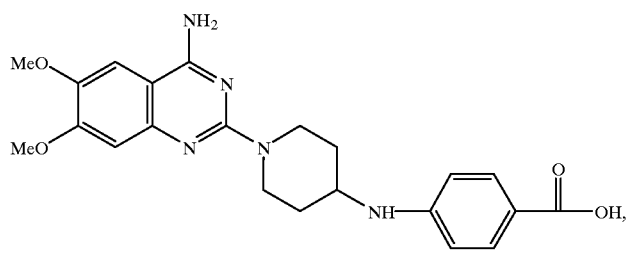

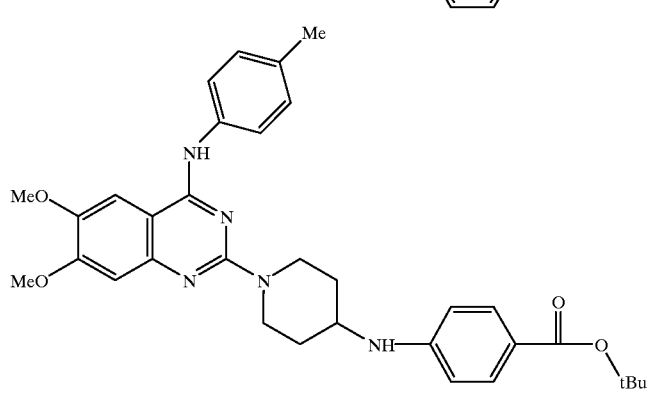

and salts, solvates and hydrates thereof.

It will be appreciated that compounds of the invention may incorporate chiral centers and therefore exist as geometric and stereoisomers. All such isomers are contemplated and are within the scope of the invention whether in pure isomeric form or in mixtures of such isomers as well as racemates.

Compounds of the invention may be prepared according to established organic synthesis techniques from starting materials and reagents that are commercially available. In a particular embodiment, compounds of the invention are prepared according to the general scheme 1.

Scheme 1

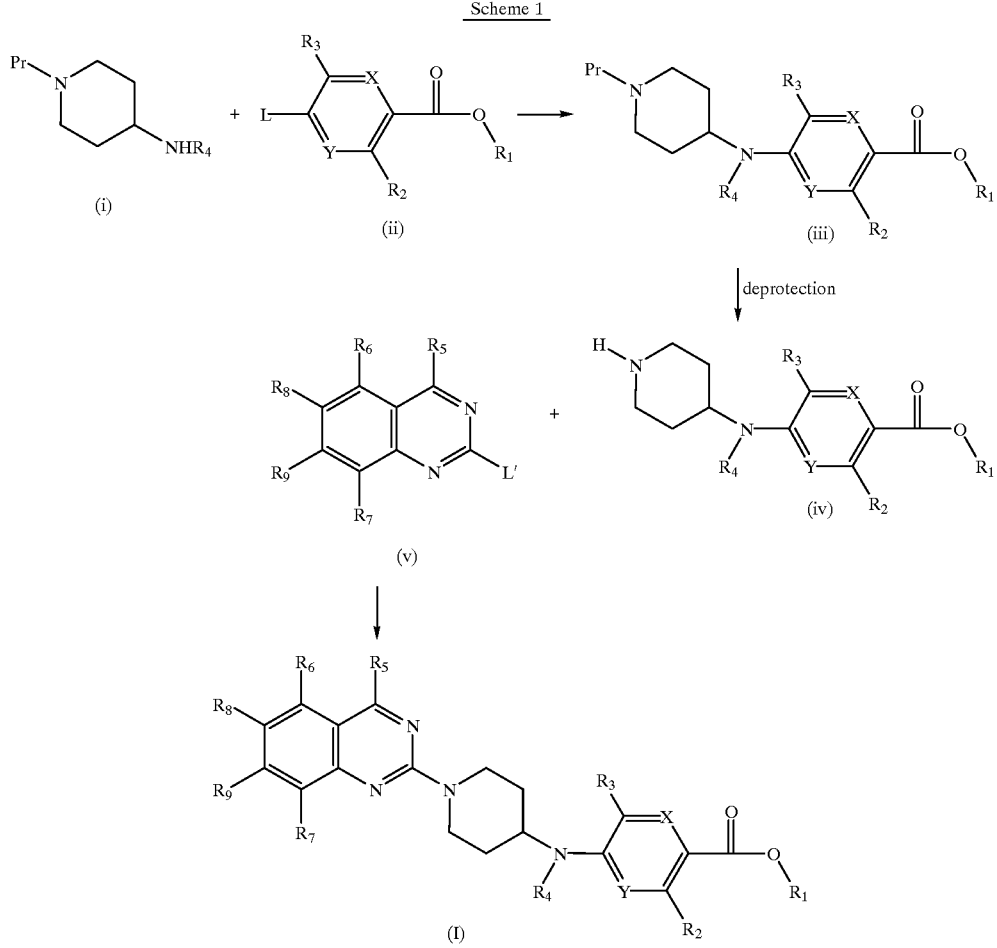

Referring to Scheme 1, compound (i) having the ring nitrogen protected with a protecting group Pr is reacted with compound (ii) having a leaving group L to form intermediate (iii). Suitable protecting groups Pr are known in the art (see Greene and Wuts, Protective Groups in Organic Chemistry, 2d edition, John Wiley and Sons, 1991) and include t-butyloxycarbonyl (Boc), fluorenyl-methyloxycarbonyl (Fmoc), 2-trimethylsilyl-ethyoxycarbonyl (Teoc), 1-methyl-1-(4-biphenylyl)ethoxycarbonyl (Bpoc), allyloxycarbonyl (Alloc), and benzyloxycarbonyl (Cbz). In a particular embodiment Pr is Boc and L is Cl. Intermediate (iii) is deprotected with a suitable reagent to give intermediate (iv) and subsequently reacted with compound (v) wherein L' is a leaving group to give final compound (I).

The piperidine and unsaturated monocycle portions of these molecules may be coupled using either aromatic nucleophilic substitution chemistries (SNAr) (Koeppe et al, WO 93/04,048; Miyamoto et al, Chem Pharm Bull, 1987, 35:2280; Kukla et al, J Med Chem, 1991, 34:746) or palladium catalyzed cross coupling methods (Wagaw et al, J Org Chem, 1996, 61:7240; Wolfe et al, J Am Chem Soc, 1996, 118:7215). As an example of the former, SNAr coupling of commercially available pyrazine carboxylic esters having a suitable leaving group (e.g. Cl) with Boc-protected 4-aminopiperidine (Mach et al, J Med Chem, 1993, 36:3707) affords the coupled intermediate. Removal of the Boc-moiety and subsequent coupling of the resulting amine hydrochloride salt with a quinazoline having a suitable leaving group at the 2-position provides compounds of the invention. The corresponding carboxylic acid is prepared by basic hydrolysis of the ester. As an example of the latter method of assembling the piperidine/unsaturated monocycle portion of the compounds, 4-bromobenzoic acid methyl ester is coupled with 4-amino-1-benzyl piperidine in the presence of Pd catalyst. The benzyl protecting group is subsequently removed and the resulting amines may be condensed with a quinazoline having a leaving group at the 2-position to afford compounds of the invention. The above scheme may also be used to prepare compounds of the invention wherein n is 0 and Z is N by substituting intermediate (i) with piperazine or mono protected piperazine.

Alternatively, compounds of the invention may be prepared by the following Scheme 2.

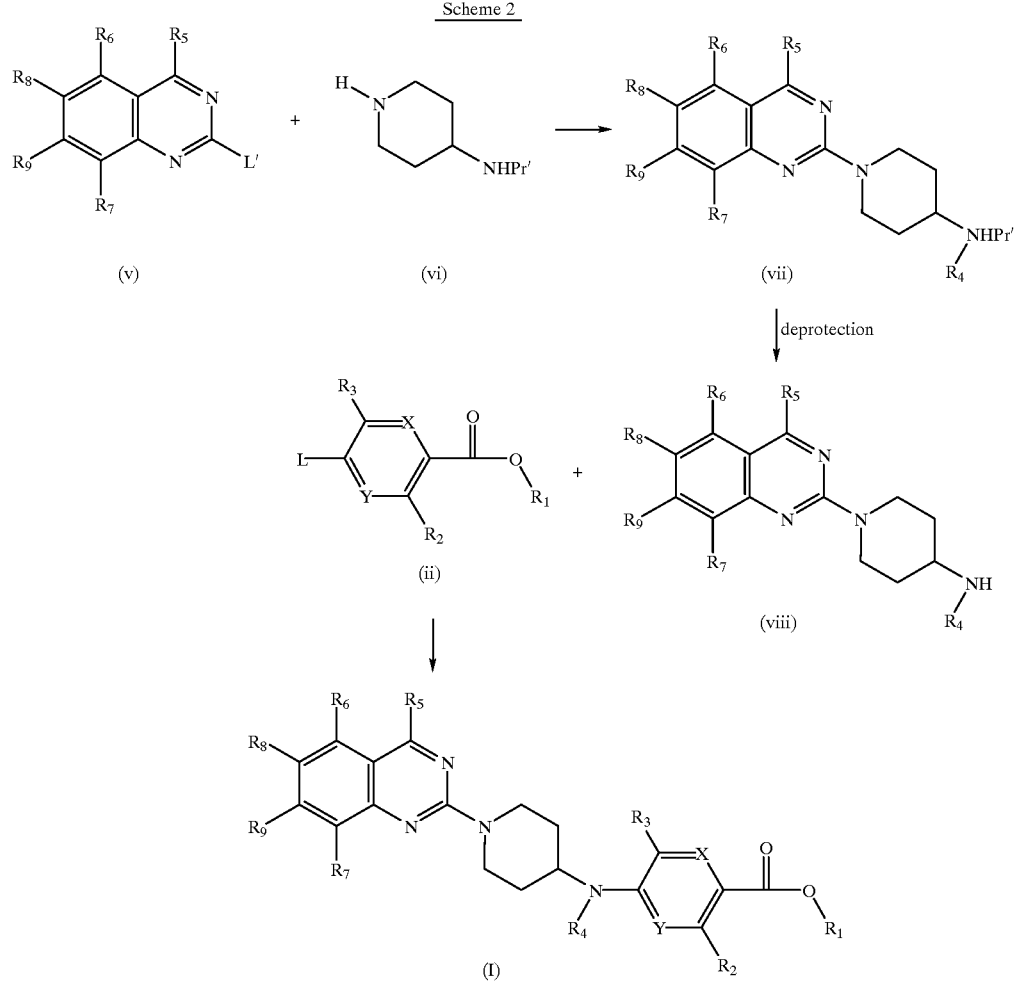

Scheme 2

Referring to Scheme 2, compound (v) is reacted with compound (vi) having a suitable amino protecting group Pr' to give intermediate (vii). Intermediate (vii) is deprotected to give intermediate (viii) which is subsequently reacted with compound (ii) to give final compound (I). Again, intermediate (vi) may be substituted with piperazine or mono protected piperazine to give compounds of the invention wherein n is 0 and Z is N. Further, it is understood that depending on the particular substituents X, Y and $R_1$ to $R_9$, further protection and deprotection steps will be employed as which are routine in the art (see Greene and Wuts supra).

Compounds of the invention are therapeutically and/or prophylactically useful for treating cancer or other diseases mediated by protein tyrosine kinases (PTKs) such as epidermal growth factor receptor kinase (EGFR kinase). Compounds of the invention are also antagonists of $\alpha_1$-adrenergic receptor and are useful against diseases mediated by activating of this receptor such as angiogenesis and cardiovascular disease. Compounds of the invention also inhibit P-selectin and L-selectin and are useful for treating conditions mediated thereby such as inflammation. Compounds of the invention are also useful for treating viral infection such as HIV, HCV, HBV, CMV, RSV, HPV and influenza.

Compounds of the invention are useful for treating microbial infections such as *K. pneumoniae, E. coli, S. aureus, E. faecalis* and *M. tuberculosis*. In a particular instance, a compound of the invention inhibited a luciferase-based bacterial transcription/translation assay with an $IC_{50}$= 12–12.5 $\mu$M. Further testing of the compound showed that the response was dose dependent and that the compound did not directly inhibit luciferase. This inhibition of transcription/translation was specific to bacteria as demonstrated by the inability of the compound to effectively inhibit a rabbit reticulocyte transcription/translation system ($IC_{50}$= 190 $\mu$M). To provide information about the site of action, its ability to inhibit incorporation of $^3$H-UTP into RNA was tested. Even at the highest doses, there was no effect on RNA synthesis, indicating that the compound worked at the translational level. Interestingly, incorporation of $^3$H amino acids into luciferase was not significantly inhibited. This result suggested that the compound functioned by allowing misincorporation of amino acids into the luciferase protein.

Accordingly there is provided a method of treating bacterial infection in a mammal comprising administering to said mammal, for example a human, an effective amount of a compound of the invention. By "effective amount" is meant an amount of compound which upon administration is capable of reducing or preventing proliferation of the bacteria or reducing or preventing symptoms associated with the bacterial infection. The actual amount of compound administered and the route of administration will depend upon the particular disease or bacteria as well as other factors such as the size, age, sex and ethnic origin of the individual being treated and is determined by routine analysis. In methods of the invention, the compound may be administered orally (including buccal, sublingual, inhalation), nasally, rectally, vaginally, intravenously, intradermally, subcutaneously and topically. Compounds will be formulated into compositions suitable for administration for example with suitable carriers, diluents, thickeners, adjuvants etc as are routine in the formulation art. Compositions of the invention may also include additional active ingredients. Dosage forms include solutions, powders, tablets, capsules, gel capsules, suppositories, topical ointments and creams and aerosols for inhalation.

Formulations for non-parenteral administration may include sterile aqueous solutions which may also contain buffers, diluents and other suitable additives. Pharmaceutically acceptable organic or inorganic carrier substances suitable for non-parenteral administration which do not deleteriously react with compounds of the invention can be used. Suitable pharmaceutically acceptable carriers include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like. The formulations can be sterilized and, if desired, mixed with auxiliary agents, e.g., lubricants, preservatives, stabilizers, wetting agents, emulsifiers, salts for influencing osmotic pressure, buffers, colorings flavorings and/or aromatic substances and the like which do not deleteriously react with compounds of the invention. Aqueous suspensions may contain substances which increase the viscosity of the suspension including, for example, sodium carboxymethylcellulose, sorbitol and/or dextran. optionally, the suspension may also contain stabilizers.

In a preferred embodiment, compounds of the invention are administered via oral delivery. Compositions for oral administration include powders or granules, suspensions or solutions in water or non-aqueous media, capsules, sachets, troches, tablets or SECs (soft elastic capsules or caplets). Thickeners, flavoring agents, diluents, emulsifiers, dispersing aids, carrier substances or binders may be desirably added to such formulations. The use of such formulations has the effect of delivering the nucleic acid to the alimentary canal for exposure to the mucosa thereof. Accordingly, the formulation can consist of material effective in protecting the compound from pH extremes of the stomach, or in releasing the compound over time, to optimize the delivery thereof to a particular mucosal site. Enteric coatings for acid-resistant tablets, capsules and caplets are known in the art and typically include acetate phthalate, propylene glycol and sorbitan monoleate.

Various methods for producing formulations for alimentary delivery are well known in the art. See, generally, Nairn, Chapter 83; Block, Chapter 87; Rudnic et al., Chapter 89; Porter, Chapter 90; and Longer et al., Chapter 91 In: *Remington's Pharmaceutical Sciences*, 18th Ed., Gennaro, ed., Mack Publishing Co., Easton, Pa., 1990. The formulations of the invention can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound should in each case be present in a concentration of about 0.5% to about 95% by weight of the total mixture, that is to say in amounts which are sufficient to achieve the desired dosage range. The formulations are prepared, for example, by extending the active compounds with solvents and/or excipients, if appropriate using emulsifying agents and/or dispersing agents, and, for example, in the case where water is used as the diluent, organic solvents can be used as auxiliary solvents if appropriate.

Compositions may be formulated in a conventional manner using additional pharmaceutically acceptable carriers or excipients as appropriate. Thus, the composition may be prepared by conventional means with additional carriers or excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrates (e.g., starch or sodium starch glycolate); or wetting agents (e.g., sodium lauryl sulfate). Tablets may be coated by methods well known in the art. The preparations may also contain flavoring, coloring and/or sweetening agents as appropriate.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

Formulations of the present invention suitable for oral administration may be presented as discrete units such as capsules, cachets or tablets each containing predetermined amounts of the active ingredients; as powders or granules; as solutions or suspensions in an aqueous liquid or a non-aqueous liquid; or as oil-in-water emulsions or water-in-oil liquid emulsions. A tablet may be made by compression or molding, optionally with one or more accessory ingredients. Compressed tablets may be prepared by compressing in a suitable machine, the active ingredients in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredients therein.

Furthermore, compounds of the invention may be used as sterilizing agents, for example as an additive or component in scrub solutions for surfaces (i.e. glassware) or in laundering compositions.

EXAMPLES

Flash column chromatography was performed using silica gel 60 (Merck Art 9385). Proton and carbon NMR spectra were recorded at 200 MHz utilizing a Varian Gemini spectrometer. Chemical shifts are in ppm ($\delta$) downfield relative to internal tetramethylsilane, and coupling constants are in Hertz.

Example 1

3-Amino-5-[1-(4-amino-6,7-dimethoxy-quinazolin-2-yl)-piperidin-4-ylamino]-6-chloro-pyrazine-2-carboxylic acid methyl ester (1)

3-Amino-5-(1-tert-butoxycarbonyl-piperidin-4-ylamino)-6-chloro-pyrazine-2-carboxylic acid methyl ester (35). Methyl 3-amino-5,6-dichloro-2-pyrazinocarboxylate (34) (1.8 g, 8.2 mmol, Aldrich) and N,N'-diisopropylethyl amine (8 mL, 45 mmol) were added sequentially to a solution of Boc-protected 4-aminopiperidine (41) (1.8 g, 9 mmol) in DMF (20 mL) at 25° C. The mixture was stirred at 25° C. for 12 h then was concentrated and the residue was diluted with a mixture of $H_2O$/EtOAc (300 mL, v/v, 50:50). The aqueous layer was extracted with more EtOAc (3×50 mL). The combined organic layer was dried ($Na_2SO_4$), filtered, and concentrated in vacuo to give a dark brown solid residue. Purification of the residue by flash column chromatography (gradient elution 5 to 25% EtOAc in hexanes) provided the title compound (2.38 g, 78%): TLC ($R_f$=0.20; 30% EtOAc/hexanes); $^1$H NMR ($CDCl_3$) δ 6.50 (br, 2H), 5.46 (d, 1H, J=7.4), 4.13 (m, 1H), 4.08 (m, 2H), 3.89 (s, 3H), 2.93 (t, 2H, J=11.7), 2.03 (d, 2H, J=12.0), 1.47 (s, 9H), 1.42 (m, 2H); $^{13}$C NMR ($CDCl_3$) δ 166.4, 155.4, 154.5, 150.6, 121.2, 110.5, 79.6, 51.8, 48.3, 42.5, 31.6, 28.3; HRMS (FAB) m/z 408.1429 (M+Na)$^+$ ($C_{16}H_{24}N_5O_4Cl$ requires 408.1415). 3-Amino-6-chloro-5-(piperidin-4-ylamino)-pyrazine-2-carboxylic acid methyl ester (36). Hydrogen chloride (25 mL, 4M in 1,4-dioxane) was added to a solution of (35) (1.8 g, 9 mmol) in EtOH (20 mL) at 25° C. The mixture was capped with a drying tube and stirred at 25° C. for 12 h. The reaction mixture was then concentrated to a pale yellow solid residue and this was used for the next step without further purification (1.8 g, quantitative yield); $^1$H NMR (DMSO) δ 9.09 (br, 1H), 7.45 (d, 1H, J=7.4), 5.12 (br, 2H), 4.05 (m, 1H), 3.72 (s, 3H), 3.31 (d, 2H, J=12.8), 2.88 (m, 2H), 1.94 (d, 2H, J=4.9), 1.86 (m, 2H); $^{13}$C NMR (DMSO) δ 165.9, 155.3, 150.7, 119.5, 108.8, 51.2, 46.2, 42.4, 27.4; HRMS (FAB) m/z 286.1079 (M)$^+$ ($C_{11}H_{16}N_5O_2Cl$ requires 286.1071); Anal. ($C_{11}H_{16}N_5O_2Cl\cdot 3.5HCl\cdot 1.75H_2O$) C, H, N.

3-Amino-5-[1-(4-amino-6,7-dimethoxy-quinazolin-2-yl)-piperidin-4-ylamino]-6-chloro-pyrazine-2-carboxylic acid methyl ester (1). 4-Amino-2-chloro-6,7-dimethoxyquinazoline (0.74 g, 3.1 mmol) was added to a solution of (36) (1.0 g, 3.2 mmol) in isoamyl alcohol (20 mL) at 25° C. The mixture was heated to 120° C. and maintained at that temperature for 12 h. The reaction mixture was then cooled to room temperature and the desired product was filtered and rinsed with acetone to give 0.75 g (49%) of the compound (1): TLC ($R_f$=0.50; 10% MeOH/$CH_2Cl_2$); $^1$H NMR ($CDCl_3$) δ 6.93 (s, 1H), 6.82 (s, 1H), 5.44 (d, 1H, J=7.8), 5.21 (br s, 2H), 4.77 (d, 2H, J=13.7), 4.19 (m, 1H), 3.97 (s, 3H), 3.92 (s, 3H), 3.90 (s, 3H), 3.12 (t, 2H, J=11.3), 2.12 (d, 2H, J=12.6), 1.56 (m, 2H); $^{13}$C NMR ($CDCl_3$) δ 166.6, 160.7, 158.4, 155.6, 155.4, 150.8, 149.6, 146.1, 121.5, 110.6, 105.8, 102.8, 101.7, 56.3, 56.1, 51.9, 48.9, 43.0, 31.8; HRMS (FAB) m/z 621.0766 (M+Cs)$^+$ ($C_{21}H_{25}N_8O_4Cl$ requires 621.0742); Anal. ($C_{21}H_{25}N_8O_4Cl\cdot 1/2HCl\cdot 1/4CH_3OH$) C, H, N.

Example 2

4-[1-(4-Amino-6,7-dimethoxy-quinazolin-2-yl)-piperidin-4-ylamino]-benzoic acid methyl ester (4)

4-(1-Benzylpiperidin-4-ylamino)benzoic Acid Methyl Ester (46). 4-Bromomethylbenzoate (4.3 g, 20 mmol) was dissolved in 40 mL of anhydrous toluene. 4-Amino-1-benzyl piperidine (4.8 mL, 22 mmol), tris(dibenzylideneacetone)-dipalladium(0) (60 mg, 0.07 mmol), (±)-2,2'-bis(diphenyl-phosphino)-1,1'-binaphthyl [(±)-BINAP] (124 mg, 0.2 mmol) and cesium carbonate (9.2 g, 28 mmol) were added sequentially at 25° C. The resulting mixture was stirred and heated to 80° C., maintained at that temperature for 12 h, then was cooled to 25° C. The reaction mixture was diluted with a mixture of MeOH/$CH_2Cl_2$ (150 mL, v/v, 50:50). The diluted mixture was filtered through celite and the filtrate was concentrated under reduced pressure. The resulting residue was partitioned between EtOAc (200 mL) and $H_2O$ (200 mL). The organic layer was dried ($Na_2SO_4$), filtered and concentrated in vacuo to give a deep yellow solid residue. Purification of the residue by flash column chromatography (gradient elution 30 to 40% EtOAc in hexanes) provided the title compound as a pale yellow solid residue (2.26 g, 35%): TLC ($R_f$=0.40; 60% EtOAc/hexanes); $^1$H NMR ($CDCl_3$) δ 7.84 (d, 2H, J=8.8), 7.31 (s, 5H), 6.52 (d, 2H, J=8.9), 4.04 (d, 1H, J=7.8), 3.84 (s, 3H), 3.53 (s, 2H), 3.40 (m, 1H), 2.85 (d, 2H, J=11.9), 2.16 (t, 2H, J=12.7), 1.99 (m, 2H), 1.52 (m, 2H); $^{13}$C NMR ($CDCl_3$) δ 167.3, 150.9, 138.2, 131.6, 129.1, 128.2, 127.1, 118.0, 111.7, 63.1, 52.1, 51.5, 49.5, 32.3; Anal. ($C_{20}H_{24}N_2O_2$) C, H, N.

4-(Piperidin-4-ylamino)benzoic Acid Methyl Ester (47). Ammonium formate (4.2 g, 66 mmol) was added to a solution of 46 (2.3 g, 6.9 mmol) in 100 mL of absolute ethanol. The mixture was purged with argon then palladium (0.8 g, 5% on activated carbon) was added. The resulting mixture was heated to 80° C. and maintained at that temperature for 12 h. After cooling to 25° C., the mixture was filtered through celite and the filtrate was concentrated under reduced pressure. The residue was cooled to 0° C., saturated $NaHCO_3$ (100 mL) was added and the resulting mixture was stirred for 30 min. The aqueous layer was extracted with EtOAc (3×100 mL). The combined organic layers were dried ($Na_2SO_4$), filtered, and concentrated in vacuo to give 1.53 g (94%) of the title compound: TLC ($R_f$=0.20; 15% MeOH/$CH_2Cl_2$); $^1$H NMR ($CDCl_3$) δ 7.85 (d, 2H, J=8.8), 6.54 (d, 2H, J=8.8), 4.08 (d, 1H, J=7.6), 3.85 (s, 3H), 3.47 (m, 1H), 3.13 (d, 2H, J=12.8), 2.72 (t, 2H, J=11.9), 2.07 (d, 2H, J=2.1), 1.37 (m, 2H); $^{13}$C NMR ($CDCl_3$) δ 167.3, 150.7, 131.6, 118.0, 111.7, 51.5, 49.9, 45.4, 33.6; Anal. ($C_{13}H_{18}N_2O_2\cdot 1/4 H_2O\cdot 1/2 CH_3OH$) C, H, N.

4-[1-(4-Amino-6,7-dimethoxy-quinazolin-2-yl)-piperidin-4-ylamino]-benzoic acid methyl ester (4). Compound 47 (0.05 g, 0.21 mmol) was added to a solution of 4-amino-2-chloro-6,7-dimethoxy quinazoline (0.05 g, 0.19 mmol) in tert-butanol (5 mL) at 25° C. The mixture was subsequently stirred at 120° C. for 12 h. The reaction mixture was then cooled to room temperature and the desired product was filtered and rinsed with acetone to give 0.07 g (83%) of the title compound: TLC ($R_f$=0.35; 5% MeOH/$CH_2Cl_2$); $^1$H NMR (DMSO) δ 12.15 (s, 1H), 8.75 (d, 2H), 7.73 (s, 1H), 7.69 (d, 2H, J=8.7), 7.51 (s, 1H), 6.66 (d, 2H, J=8.4), 6.57 (d, 1H, J=7.3), 4.52 (d, 2H, J=13.2), 3.87 (s, 3H), 3.83 (s, 3H), 3.82 (m, 1H), 3.73 (s, 3H), 3.43 (m, 2H), 2.05 (m, 2H), 1.44 (m, 2H); $^{13}$C NMR ($CDCl_3$) δ 166.3, 161.4, 155.2, 151.7, 151.0, 146.7, 136.0, 131.0, 115.8, 111.3, 104.9, 101.6, 99.2, 56.2, 56.0, 51.2, 47.9, 43.4, 31.0; Anal. ($C_{23}H_{27}N_5O_4\cdot 1HCl$) C, H, N.

Example 3

4-[1-(4-Amino-6,7-dimethoxy-quinazolin-2-yl)-piperidin-4-ylamino]-benzoic acid tert-butyl ester (5)

4-(1-Benzylpiperidin-4-ylamino)benzoic Acid tert-Butyl Ester (48). Sodium tert-butoxide (5.6 g, 58 mmol) was added to a solution of 4-bromo methyl benzoate (4.3 g, 20 mmol) in 40 mL of anhydrous toluene at 25° C. The resulting mixture was heated to 80° C. and stirred for 15 min. 4-Amino-1-benzyl piperidine (4.8 mL, 22 mmol), tris (dibenzylideneacetone)-dipalladium(0) (60 mg, 0.07 mmol) and (±)-2,2'-bis(diphenyl-phosphino)-1,1'-binaphthyl [(±)-BINAP] (124 mg, 0.2 mmol) were added sequentially. The reaction mixture was maintained at 80° C. for 12 h then was cooled to 25° C. and diluted with a mixture of MeOH/ CH$_2$Cl$_2$ (150 mL, v/v, 50:50). The diluted mixture was filtered through celite and the filtrate was concentrated under reduced pressure. The resulting residue was partitioned between CH$_2$Cl$_2$ (150 mL) and H$_2$O (150 mL). The organic layer was dried (Na$_2$SO$_4$), filtered and concentrated in vacuo to give a deep yellow solid residue. This residue was stirred for 30 min with a mixture of EtOAc/hexanes (100 mL, 30/70, v/v) and the desired product was filtered as a yellowish powder (3.57 g, 49%): TLC (R$_f$=0.51; 50% EtOAc/ hexanes); $^1$H NMR (CDCl$_3$) δ 7.79 (d, 2H, J=8.7), 7.31 (s, 5H), 6.51 (d, 2H, J=8.8), 3.90 (m, 1H), 3.52 (s, 2H), 2.85 (d, 2H, J=12.1), 2.15 (t, 2H, J=11.5), 1.99 (m, 2H), 1.56 (s, 9H), 1.47 (m, 2H); $^{13}$C NMR (CDCl$_3$) δ 166.1, 150.5, 138.3, 131.4, 129.1, 128.2, 127.1, 120.1, 111.6, 79.8, 63.1, 52.2, 49.6, 32.3, 28.3; Anal. (C$_{23}$H$_{30}$N$_2$O$_2$·1/2 H$_2$O) C, H, N.

4-(Piperidin-4-ylamino)benzoic Acid tert-Butyl Ester (49). Ammonium formate (4.2 g, 66 mmol) was added to a solution of (48) (2.7 g, 7.3 mmol) in 120 mL of absolute ethanol. The mixture was purged with argon then palladium (1 g, 5% on activated carbon) was added. The resulting mixture was heated to 80° C. and maintained at that temperature for 12 h. After cooling to 25° C., the mixture was filtered through celite and the filtrate was concentrated in vacuo. The residue was cooled to 0° C., saturated Na$_2$CO$_3$ (100 mL) was added, and the resulting mixture was stirred for 30 min. The aqueous layer was extracted with EtOAc (3×100 mL). The combined organic layers were dried (Na$_2$SO$_4$), filtered, and concentrated in vacuo to give 1.85 g (92%) of the title compound: TLC (R$_f$=0.20; 10% MeOH/ CH$_2$Cl$_2$); $^1$H NMR (CDCl$_3$) δ 7.80 (d, 2H, J=8.7), 6.53 (d, 2H, J=8.8), 4.10 (m, 1H), 3.40 (m, 1H), 3.11 (d, 2H, J=12.7), 2.70 (t, 2H, J=11.9), 2.04 (m, 2H), 1.79 (s, 1H), 1.56 (s, 9H), 1.35 (m, 2H); $^{13}$C NMR (CDCl$_3$) δ 166.0, 150.3, 131.2, 119.9, 111.5, 79.6, 49.9, 45.3, 33.5, 28.2; Anal. (C$_{16}$H$_{24}$N$_2$O$_2$·1/4 H$_2$O) C, H, N.

4-[1-(4-Amino-6,7-dimethoxy-quinazolin-2-yl)-piperidin-4-ylamino]-benzoic acid tert-butyl ester (5). Compound 49 (0.57 g, 2.1 mmol) was added to a solution of 4-amino-2-chloro-6,7-dimethoxy quinazoline (0.45 g, 1.9 mmol) in isoamyl alcohol (3-methyl-1-butanol) (20 mL) at 25° C. The mixture was stirred at 120° C. for 12 h. The reaction mixture was cooled to room temperature and the desired product was filtered and rinsed with acetone to give 0.57 g (59%) of the title compound: TLC (R$_f$=0.41; 80% EtOAc/hexanes); $^1$H NMR (DMSO) δ 12.20 (br s, 1H), 8.66 (br, 2H), 7.76 (s, 1H), 7.66 (d, 2H, J=8.7), 7.53 (s, 1H), 6.67 (d, 2H, J=8.7), 6.51 (d, 1H, J=7.4), 4.56 (d, 2H, J=13.6), 3.90 (s, 3H), 3.86 (s, 3H), 3.76 (m, 1H), 3.46 (m, 2H), 2.07 (d, 2H, J=11.1), 1.52 (s, 9H), 1.44 (m, 2H); $^{13}$C NMR (DMSO) δ 165.3, 161.4, 155.3, 151.4, 151.1, 146.8, 136.4, 131.0, 117.8, 111.3, 105.0, 101.6, 99.2, 79.1, 56.3, 56.1, 48.0, 43.4, 31.0, 28.1; HRMS (FAB) m/z 480.2616 (M+H)$^+$ (C$_{26}$H$_{33}$N$_5$O$_4$ requires 480.2611); Anal. (C$_{26}$H$_{33}$N$_5$O$_4$·1HCl) C, H, N.

Example 4

4-[1-(4-Amino-6,7-dimethoxyquinazolin-2-yl) piperidin-4-ylamino]benzoic acid (22).

A solution of 4-[1-(4-Amino-6,7-dimethoxy-quinazolin-2-yl)-piperidin-4-ylamino]-benzoic acid tert-butyl ester (5) (0.55 g, 1.15 mmol) in HCl (10 mL, 1M in 1,4-dioxane) was capped with a drying tube and stirred at 25° C. for 12 h. The reaction mixture was concentrated to give a pale yellow solid residue (0.52 g, 91.3%); $^1$H NMR (DMSO) δ 12.08 (br s, 2H), 8.85 (br s, 1H), 8.64 (br s, 1H), 7.73 (s, 1H), 7.67 (d, 2H, J=8.7), 7.48 (s, 1H), 6.65 (d, 2H, J=8.8), 6.47 (br s, 1H), 4.51 (d, 2H, J=13.2), 3.88 (s, 3H), 3.84 (s, 3H), 3.71 (m, 1H), 3.35 (t, 2H, J=12.0), 2.06 (d, 2H, J=10.4), 1.47 (m, 2H); $^{13}$C NMR (DMSO) δ 167.8, 161.6, 155.7, 151.7, 151.1, 147.1, 136.2, 131.6, 117.1, 111.6, 105.0, 101.7, 99.1, 56.5, 56.4, 48.1, 43.6, 31.2; HRMS (FAB) m/z 424.2003 (M+H)$^+$ (C$_{22}$H$_{25}$N$_5$O$_4$ requires 424.1985); Anal. (C$_{22}$H$_{25}$N$_5$O$_4$·2HCl) C, H, N.

Example 5

4-[1-(6,7-Dimethoxy-4-p-tolylaminoquinazolin-2-yl) piperidin-4-ylamino]benzoic acid tert-butyl ester (16)

2-chloro-6,7-dimethoxy-N-(4-methylphenyl)-4-quinazolinamine (0.099 g, 0.3 mmol) prepared according to the procedures described in Gazit et al (Bioorg Med Chem, 1996, 4:1203) was added to a solution of (49) (0.10 g, 0.37 mmol) in n-pentanol (5 mL) at 25° C. The mixture was heated to 120° C. and maintained at that temperature for 12 h. The reaction mixture was then cooled to room temperature and the desired product was filtered and rinsed with acetone to give 0.146 g (85.3%) of the title compound: TLC (R$_f$=0.40; 5% MeOH/CH$_2$Cl$_2$); $^1$H NMR (DMSO) δ 12.41 (br s, 1H), 10.71 (br s, 1H), 8.08 (s, 1H), 7.63 (d, 2H, J=8.7), 7.57 (s, 1H), 7.55 (d, 2H, J=8.3), 7.24 (d, 2H, J=8.3), 6.63 (d, 2H, J=8.8), 6.44 (d, 1H, J=6.9), 4.41 (d, 2H, J=12.9), 3.91 (s, 3H), 3.89 (s, 3H), 3.73 (m, 1H), 3.42 (m, 2H), 2.31 (s, 3H), 2.03 (d, 2H, J=10.8), 1.49 (s, 9H), 1.41 (m, 2H); $^{13}$C NMR (DMSO) δ 165.2, 157.2, 155.2, 151.3, 150.7, 146.9, 136.6, 134.7, 130.9, 129.0, 124.0, 117.7, 111.2, 104.6, 102.3, 99.3, 79.0, 56.5, 56.1, 47.9, 43.7, 30.8, 28.0, 20.6; HRMS (FAB) m/z 570.3070 (M+H)$^+$ (C$_{33}$H$_{39}$N$_5$O$_4$ requires 570.3080); Anal. (C$_{33}$H$_{39}$N$_5$O$_4$·1HCl) C, H, N.

Example 6

3-Amino-5-[1-(4-amino-6,7-dimethoxy-quinazolin-2-yl)-piperidin-4-ylamino]-pyrazine-2-carboxylic acid methyl ester (2)

3-Amino-5-(1-benzyl-piperidin-4-ylamino)-6-chloro-pyrazine-2-carboxylic acid methyl ester (37). 4-Amino-1-benzylpiperidine (45) (1 mL, 5 mmol) and N,N'-diisopropylethyl amine (4.5 mL, 25 mmol) were added sequentially to a solution of methyl 3-amino-5, 6-dichloro-2-pyrazinocarboxylate (34) (1.1 g, 4.8 mmol) in DMF (10 mL) at 25° C. The mixture was stirred at 25° C. for 12 h. The reaction mixture was then concentrated and the residue was diluted with a mixture of sat. NaCl (aq)/EtOAc (100 mL, v/v, 50:50). The aqueous layer was extracted with more EtOAc (3×50 mL). The combined organic layers were dried (Na$_2$SO$_4$), filtered, and concentrated in vacuo to give a dark brown oily residue. Purification of the residue by flash column chromatography (gradient elution 1 to 5% CH$_3$OH/ CH$_2$Cl$_2$) provided the title compound (1.82 g, quantitative yield): TLC (R$_f$=0.32; 5% CH$_3$OH/CH$_2$Cl$_2$); $^1$H NMR (CDCl$_3$) δ 7.31 (s, 5H), 5.42 (d, 1H, J=7.4), 3.90 (m, 1H), 3.88 (s, 3H), 3.53 (s, 2H), 2.84 (d, 2H, J=11.8), 2.17 (t, 2H, J=11.2), 1.99 (d, 2H, J=9.3), 1.60 (m, 2H); $^{13}$C NMR (CDCl$_3$) δ 166.5, 155.6, 150.9, 138.4, 128.9, 128.2, 127.0, 121.4, 110.0, 63.0, 52.0, 51.7, 48.2, 31.9; HRMS (FAB) m/z 376.1549 (M)$^+$ (C$_{18}$H$_{22}$N$_5$O$_2$Cl requires 376.1540); Anal. (C$_{18}$H$_{22}$N$_5$O$_2$Cl) C, H, N.

3-Amino-5-(piperidin-4-ylamino)-pyrazine-2-carboxylic acid methyl ester (38). Ammonium formate (3.5 g, 48 mmol) was added to a solution of (37) (1.8 g, 4.8 mmol) in 60 mL of absolute ethanol. The mixture was purged with argon then palladium (0.5 g, 5% on activated carbon) was added. The resulting mixture was heated at 80° C. for with argon then palladium (0.5 g, 5% on activated carbon) was added. The resulting mixture was heated at 80° C. for 12 h then was cooled to 25° C. and filtered through celite. The filtrate was concentrated in vacuo and the residue was cooled to 0° C. Saturated $Na_2CO_3$ (100 mL) was added, and the resulting mixture was stirred for 30 min. The aqueous layer was extracted with EtOAc (3×50 mL) and the combined organic layers were dried ($Na_2SO_4$), filtered and concentrated in vacuo to give 1.3 g (quantitative yield) of the title compound: TLC ($R_f$=0.24; 10% MeOH/$CH_2Cl_2$); $^1$H NMR (DMSO) δ 7.86 (d, 1H, J=6.9), 7.28 (s, 1H), 7.10 (br s, 2H), 3.95 (m, 1H), 3.69 (s, 3H), 3.26 (d, 2H, J=12.8), 2.92 (t, 2H, J=9.8), 2.00 (d, 2H, J=12.0), 1.70 (m, 2H); $^{13}$C NMR (DMSO) δ 167.0, 156.4, 154.6, 122.8, 109.8, 50.9, 44.4, 41.8, 27.9; HRMS (FAB) m/z 252.1466 (M+H)$^+$ ($C_{11}H_{17}N_5O_2$ requires 252.1461).

3-Amino-5-[1-(4-amino-6,7-dimethoxy-quinazolin-2-yl)-piperidin-4-ylamino]-pyrazine-2-carboxylic acid methyl ester (2). Compound (38) (2.5 mmol) was added to a solution of 4-amino-2-chloro-6,7-dimethoxyquinazoline (0.6 g, 2.5 mmol) in isoamyl alcohol (20 mL) at 25° C. The mixture was stirred at 120° C. for 12 h. The reaction mixture was then cooled to room temperature and the desired product was filtered and rinsed with acetone to give 0.70 g (65%) of the title compound: TLC ($R_f$=0.30; 10% $CH_3OH$/$CH_2Cl_2$); $^1$H NMR (DMSO) δ 7.59 (d, 1H, J=7.7), 7.41 (s, 1H), 7.22 (s, 1H), 7.15 (br s, 4H), 6.73 (s, 1H), 4.63 (d, 2H, J=13.2), 4.10 (m, 1H), 3.82 (s, 3H), 3.77 (s, 3H), 3.69 (s, 3H), 2.99 (t, 2H, J=9.8), 1.90 (d, 2H, J=10.0), 1.39 (m, 2H); $^{13}$C NMR (DMSO) δ 167.0, 31.2; HRMS (FAB) m/z 455.2143 (M+H)$^+$ ($C_{21}H_{26}N_8O_4$ requires 455.2155); Anal. ($C_{21}H_{26}N_8O_4$·1/2$H_2O$·1/2$CH_3OH$) C, H, N.

Example 7

6-[1-(4-Amino-6,7-dimethoxy-quinazolin-2-yl)-piperidin-4-ylamino]-nicotinic acid methyl ester (3)

6-(1-Benzyl-piperidin-4-ylamino)-nicotinic acid methyl ester (39). 4-Amino-1-benzylpiperidine (30 mL, 150 mmol) and N,N'-diisopropylethyl amine (25 mL, 150 mmol) were added sequentially to a solution of methyl 2-chloropyridine-5-carboxylate (5 g, 29.1 mmol) in DMF (20 mL) at 25° C. The mixture was stirred at 75° C. for 12 h. The reaction mixture was then evaporated and diluted with a mixture of sat. NaCl (aq)/EtOAc (100 mL, v/v, 50:50). The aqueous layer was extracted with more EtOAc (3×50 mL). The combined organic layers were dried ($Na_2SO_4$), filtered, and concentrated in vacuc to give a yellow oily residue. Purification of the residue by flash column chromatography (gradient elution 70 to 80% EtOAc/hexanes) provided the title compound (4.3 g, 45.4%): TLC ($R_f$=0.20; 60% EtOAc/hexanes); $^1$H NMR (CDCl$_3$) δ 8.73 (d, 1H, J=2.1), 7.95 (m, 1H), 7.30 (m, 5H), 6.32 (d, 1H, J=8.8), 5.01 (d, 1H, J=7.8), 3.85 (s, 3H), 3.71 (m, 1H), 3.52 (s, 2H), 2.85 (m, 2H), 2.18 (m, 2H), 1.20 (m, 2H), 1.57 (m, 2H); $^{13}$C NMR (CDCl$_3$) δ 166.4, 160.1, 151.6, 138.3, 129.0, 128.1, 127.6, 127.0, 115.0, 105.8, 63.0, 52.0, 51.4, 48.4, 32.3; HRMS (FAR) m/z 326.1879 (M+H)$^+$ ($C_{19}H_{23}N_3O_2$ requires 326.1869).

6-(Piperidin-4-ylamino)-nicotinic acid methyl ester (40). Ammonium formate (4.9 g, 67.2 mmol) was added to a solution of (39) (4.2 g, 12.9 mmol) in 100 mL of absolute ethanol. The mixture was purged with argon then palladium (0.9 g, 5% on activated carbon) was added. The resulting mixture was heated at 80° C. and maintained at that temperature for 12 h. After cooling to 25° C., the mixture was filtered through celite and the filtrate was concentrated in vacuo. The residue was cooled to 0° C. and saturated $Na_2CO_3$ (100 mL) was added. The resulting mixture was stirred for 30 min at 0° C. then was extracted with EtOAc (3×50 mL). The combined organic layers were dried ($Na_2SO_4$), filtered, and concentrated in vacuo to give 2.6 g (86%) of the title compound; $^1$H NMR (CDCl$_3$) δ 8.55 (s, 1H), 7.78 (d, 1H, J=8.9), 7.35 (d, 1H, J=7.3), 6.49 (d, 1H, J=8.9), 3.77 (m, 4H), 3.12 (s, 1H), 2.94 (m, 2H), 2.52 (m, 2H), 1.82 (m, 2H), 1.29 (m, 2H); $^{13}$C NMR (CDCl$_3$) δ 165.7, 160.2, 150.8, 136.7, 112.7, 107.5, 51.1, 48.0, 45.0, 33.0; HRMS (FAB) m/z 236.1392 (M+H)$^+$ ($C_{12}H_{17}N_3O_2$, requires 236.1399).

6-[1-(4-Amino-6,7-dimethoxy-quinazolin-2-yl)-piperidin-4-ylamino]-nicotinic acid methyl ester (3). Compound (40) (1.18 g, 5 mmol) was added to a solution of 4-amino-2-chloro-6,7-dimethoxyquinazoline (1.0 g, 4 mmol) in isoamyl alcohol (10 mL) at 25° C. The mixture was stirred at 120 C. for 12 h. The reaction mixture was then cooled to room temperature and the desired product was filtered and rinsed with acetone to give 1.5 g (68%) of the title compound; $^1$H NMR (DMSO) δ 12.37 (s, 1H), 8.74 (d, 2H, J=6.3), 8.57 (d, 1H, J=2.2), 7.80 (m, 1H), 7.76 (s, 1H), 7.62 (s, 1H), 7.60 (d, 1H, J=8.8), 6.56 (d, 1H, J=8.9), 4.57 (m, 2H), 4.20 (m, 1H), 3.86 (s, 3H), 3.84 (s, 3H), 3.76 (s, 3H), 3.42 (m, 2H), 2.03 (m, 2H), 1.51 (m, 2H); $^{13}$C NMR (DMSO) δ 165.6, 161.3, 160.2, 155.1, 151.0, 150.6, 146.6, 136.8, 136.4, 113.1, 107.9, 105.2, 101.5, 99.3, 56.2, 55.9, 51.2, 46.6, 43.4, 30.9; HRMS (FAB) m/z 439.2083 (M+H)$^+$ ($C_{22}H_{26}N_6O_4$ requires 439.2094); Anal. ($C_{22}H_{26}N_6O_4$·1HCl) C, H, N.

Example 8

4-[1-(4-Amino-6,7-dimethoxyquinazolin-2-yl) piperidin-4-ylamino]-3-nitrobenzoic acid tert-butyl ester (6)

4-Chloro-3-nitrobenzoic acid tert-butyl ester (42). A solution of 4-chloro-3-nitrobenzoylchloride (8.80 g, 40 mmol) in $CH_2Cl_2$ (20 mL) was added to a solution of tert-butyl alcohol (7.6 mL, 80 mmole) and pyridine (6.6 mL, 80 mmole) at 25° C. The mixture was stirred at 25° C. for 12 h then $H_2O$ (30 mL) was added. The aqueous solution was extracted with ethyl ether (3×100 mL). The combined organic layers were dried ($Na_2SO_4$), filtered, and concentrated in vacuo to give a yellowish solid residue. Purification of the residue by flash column chromatography (gradient elution 0 to 15% EtOAc/hexanes) provided the title compound (8.11 g, 79%): TLC ($R_f$=0.50; 15% EtOAc/hexanes); $^1$H NMR (CDCl$_3$) δ 8.41 (s, 1H), 8.13 (d, 1H, J=8.0), 7.63 (d, 1H, J=8.3), 1.63 (s, 9H); $^{13}$C NMR (CDCl$_3$)δ 162.4, 147.6, 133.2, 131.6, 130.5, 126.0, 124.4, 82.6, 27.8; Anal. ($C_{11}H_{12}N_1O_4Cl$) C, H, N.

4-(4-tert-Butoxycarbonyl-2-nitrophenylamino) piperidine-1-carboxylic acid tert-butyl ester (43). Boc-protected 4-aminopiperidine (41) (4.0 g, 20 mmol) and N,N'-diisopropylethyl amine (3.5 mL, 20 mmol) was added to a solution of (42) (1.94 g, 7.55 mmol) in DMF (40 mL) at 25° C. The mixture was heated to 110° C. and maintained at that temperature for 24 h. The reaction mixture was then cooled to room temperature and was concentrated in vacuo to give a gummy residue. Purification of the residue by flash column chromatography (gradient elution 0 to 15% EtOAc/hexanes) provided the title compound (1.75 g, 55%): TLC ($R_f$=0.22; 15% EtOAc/hexanes); $^1$H NMR (CDCl$_3$) δ 8.81 (s, 1H), 8.36 (d, 1H, J=7.3), 8.02 (d, 1H, J=8.3), 6.88 (d, 1H, J=9.3), 4.05 (d, 2H, J=13.3), 3.73 (m, 1H), 3.06 (t, 2H, J=11.2), 2.07 (d, 2H, J=11.1), 1.59 (s, 9H), 1.45 (s, 9H); $^{13}$C NMR (CDCl$_3$) δ 164.2, 154.6, 146.3, 136.4, 131.3, 129.5, 119.3, 113.4, 81.4, 80.0, 49.6, 42.0, 31.6, 28.4, 28.2; HRMS (FAB) m/z 422.2304 (M+H)$^+$ (C$_{21}$H$_{31}$N$_3$O$_6$ requires 422.2291).

3-Nitro-4-(piperidin-4-ylamino)benzoic acid tert-butyl ester (44). Hydrogen chloride (1 mL, 4M in 1,4-dioxane) was added to a solution of (43) (0.1 g, 0.24 mmol) in 1,4-dioxane (5 mL) at 25° C. After 12 h, the reaction mixture was evaporated to a bright yellow solid residue which was basicified with NaOH(aq). The aqueous solution was extracted with EtOAc (3×50 mL). The combined organic layers were dried (Na$_2$SO$_4$), filtered, and concentrated in vacuo to give a yellow oily residue which was used in the next reaction without further purification (0.045 g, 59%): TLC (R$_f$=0.20; 15% MeOH/CH$_2$Cl$_2$); $^1$H NMR (CDCl$_3$) δ 8.74 (s, 1H), 8.33 (d, 1H, J=5.4), 7.94 (d, 1H, J=8.8), 6.82 (d, 1H, J=8.8), 3.60 (m, 1H), 3.12 (d, 2H, J=11.3), 2.74 (t, 2H, J=11.7), 2.21 (s, 2H), 2.05 (d, 2H, J=12.5), 1.53 (s, 9H); $^{13}$C NMR (CDCl$_3$) δ 164.2, 146.3, 136.2, 131.1, 129.4, 118.9, 113.4, 81.2, 49.8, 44.8, 32.9, 28.2; HRMS (FAB) m/z 322.1750 (M+H)$^+$ (C$_{16}$H$_{23}$N$_3$O$_4$ requires 322.1761); Anal. (C$_{16}$H$_{23}$N$_3$O$_4$·1HCl·1CH$_3$OH) C, H, N.

4-[1-(4-Amino-6,7-dimethoxyquinazolin-2-yl)piperidin-4-ylamino]-3-nitrobenzoic acid tert-butyl ester (6). 4-Amino-2-chloro-6,7-dimethoxyquinazoline (0.08 g, 0.33 mmol) was added to a solution of (44) (0.11 g, 0.35 mmol) in n-pentanol (5 mL) at 25° C. The mixture was heated to 120° C. and maintained at that temperature for 12 h. The reaction mixture was then cooled to room temperature and the desired product was filtered and rinsed with acetone to give 0.11 g (64%) of the title compound: TLC (R$_f$=0.30; 5% MeOH/CH$_2$Cl$_2$); $^1$H NMR (DMSO) δ 12.23 (s, 1H), 8.89 (s, 1H), 8.65 (s, 1H), 8.56 (s, 1H, J=2.0), 8.23 (d, 1H, J=7.8), 7.94 (d, 1H, J=9.2), 7.74 (s, 1H), 7.55 (s, 1H), 7.34 (d, 1H, J=9.3), 4.62 (d, 2H, J=13.3), 4.15 (m, 1H), 3.87 (s, 3H), 3.84 (s, 3H), 3.35 (t, 2H, J=11.6), 2.10 (d, 2H, J=11.3), 1.74 (m, 2H), 1.53 (s, 9H); $^{13}$C NMR (DMSO) δ 163.5, 161.4, 155.2, 151.2, 146.8, 146.2, 136.3, 135.8, 130.6, 128.2, 117.9, 115.1, 104.9, 101.6, 99.1, 80.8, 56.2, 56.0, 48.8, 43.5, 30.5, 27.8; HRMS (FAB) m/z 525.2456 (M+H)$^+$ (C$_{26}$H$_{32}$N$_6$O$_6$ requires 525.2454); Anal. (C$_{26}$H$_{32}$N$_6$O$_6$·1HCl) C, H, N.

Example 9

4-[1-(6,7-Dimethoxyquinazolin-2-yl)piperidin-4-ylamino]benzoic acid tert-butyl ester (13)

4-[1-(6,7-Dimethoxyquinazolin-2-yl)piperidin-4-ylamino]benzoic acid tert-butyl ester (13). 4-(Piperidin-4-ylamino)benzoic acid tert-butyl ester (49) (0.15 g, 0.54 mmol), was added to a solution of 2-chloro- 6,7-dimethoxyquinazoline (0.07 g, 0.31 mmol) in n-pentanol (5 mL) at 25° C. The mixture was stirred at 120° C. for 12 h. The reaction mixture was then cooled to room temperature and concentrated to a brown solid residue. Purification of the residue by flash column chromatography (gradient elution 30 to 40% EtOAc/hexanes) provided the title compound (0.03 g, 18%): TLC (R$_f$=0.50; 50% EtOAc/hexanes); $^1$H NMR (DMSO) δ 8.93 (s, 1H), 7.62 (d, 2H, J=8.7), 7.20 (s, 1H), 6.91 (s, 1H), 6.61 (d, 2H, J=8.8), 6.37 (d, 1H, J=7.9), 4.67 (d, 2H, J=13.2), 3.89 (s, 3H), 3.82 (s, 3H), 3.65 (m, 1H), 3.16 (t, 2H, J=11.5), 1.97 (d, 2H, J=10.4), 1.48 (s, 9H), 1.36 (m, 2H); $^{13}$C NMR (DMSO) δ 165.3, 158.6, 158.4, 156.1, 151.5, 149.3, 146.5, 130.9, 117.5, 113.9, 111.1, 105.4, 104.4, 78.9, 55.8, 55.6, 48.9, 42.5, 31.2, 28.0; HRMS (FAB) m/z 465.2503 (M+H)$^+$ (C$_{26}$H$_{32}$N$_4$O$_4$ requires 465.2494); Anal. (C$_{26}$H$_{32}$N$_4$O$_4$·1/4HCl·1/4H$_2$O) C, H, N.

Example 10

4-[1-(4,6,7-Trimethoxyquinazolin-2-yl)piperidin-4-ylamino]benzoic acid tert-butyl ester (14); and 4-[1-(6,7-Dimethoxy-4-oxo-3,4-dihydroquinazolin-2-yl)piperidin-4-ylamino]benzoic acid tert-butyl ester (15)

2-Chloro-4,6,7-trimethoxyquinazoline (QME). Sodium methoxide (0.12 g, 2.2 mmole) was added to a solution of 2,4-dichloro-6,7-dimethoxyquinazoline (0.52 g, 2 mmol) in methanol (20 mL) at 25° C. The mixture was stirred at 25° C. for 12 h and was concentrated in vacuo to give a white solid residue. Purification of the residue by flash column chromatography (gradient elution 30 to 60% EtOAc/hexanes) provided the title compound (0.51 g, quantitative yield): TLC (R$_f$=0.50; CH$_2$Cl$_2$); $^1$H NMR (CDCl$_3$) δ 7.33 (s, 1H), 7.21 (s, 1H), 4.20 (s, 3H), 4.01 (s, 6H); $^{13}$C NMR (CDCl$_3$) δ 166.9, 156.1, 154.3, 149.8, 149.5, 109.0, 106.2, 101.4, 56.4, 56.3, 55.0; HRMS (FAB) m/z 255.0531 (M+H)$^+$ (C$_{11}$H$_{11}$N$_2$O$_3$Cl requires 255.0536); Anal. (C$_{11}$H$_{11}$N$_2$O$_3$Cl·1/2H$_2$O·1/4CH$_3$OH) C, H, N.

4-[1-(6,7-Dimethoxy-4-oxo-3,4-dihydroquinazolin-2-yl)piperidin-4-ylamino]benzoic acid tert-butyl ester (15). 4-(Piperidin-4-ylamino)benzoic Acid tert-Butyl Ester (49) (0.47 mmol) was added to a solution of 2-chloro-4,6,7-trimethoxy-quinazoline (0.1 g, 0.39 mmol) in n-pentanol (5 mL) at 25° C. The mixture was stirred at 120° C. for 12 h. The reaction mixture was then cooled to room temperature and the desired product was filtered and rinsed with acetone to give 0.06 g (32%) of (15): TLC (R$_f$=0.30; 5% CH$_3$OH/CH$_2$Cl$_2$); $^1$H NMR (DMSO) δ 11.24 (s, 1H), 7.61 (d, 2H, J=8.4), 7.26 (s, 1H), 6.76 (s, 1H), 6.60 (d, 2H, J=8.7), 6.36 (d, 1H, J=7.8), 4.24 (d, 2H, J=13.6), 3.83 (s, 3H), 3.78 (s, 3H), 3.60 (m, 1H), 3.09 (m, 2H), 1.94 (d, 2H, J=10.4), 1.48 (s, 9H), 1.40 (m, 2H) $^{13}$C NMR (DMSO) δ 165.2, 162.4, 154.9, 151.4, 150.1, 146.7, 145.6, 130.9, 117.6, 111.2, 109.2, 106.0, 105.3, 78.9, 55.7, 55.5, 48.4, 43.9, 30.9, 28.0; HRMS (FAB) m/z 481.2444 (M+H)$^+$ (C$_{26}$H$_{32}$N$_4$O$_5$ requires 481.2443); Anal. (C$_{26}$H$_{32}$N$_4$O$_5$·1/2HCl) C, H, N.

4-[1-(4,6,7-Trimethoxyquinazolin-2-yl)piperidin-4-ylamino]benzoic acid tert-butyl ester (14). The filtrate was concentrated and purified by flash column chromatography (gradient elution 30 to 40% EtOAc/hexanes) provided (14) (0.09 g, 45%): TLC (R$_f$=0.50; 40% EtOAc/hexanes); $^1$H NMR (DMSO) δ 7.62 (d, 2H, J=8.7), 7.12 (s, 1H), 6.87 (s, 1H), 6.61 (d, 2H, J=8.8), 6.37 (d, 1H, J=7.9), 4.65 (d, 2H, J=13.2), 4.02 (s, 3H), 3.86 (s, 3H), 3.79 (s, 3H), 3.60 (m, 1H), 3.13 (m, 2H), 1.95 (m, 2H), 1.49 (s, 9H), 1.38 (m, 2H): $^{13}$C NMR (DMSO) δ 165.4, 157.5, 155.4, 151.6, 150.2, 149.8, 145.8, 131.0, 117.5, 111.2, 104.9, 103.4, 101.8, 56.3, 56.0, 55.7, 53.5, 49.0, 31.3, 28.1; Anal. (C$_{27}$H$_{34}$N$_4$O$_5$·1/4HCl·1/2CH$_3$OH) C, H, N.

Example 11

4-[1-(4-Aminoquinazolin-2-yl)piperidin-4-ylamino]benzoic acid tert-butyl ester (17)

4-[1-(4-Aminoquinazolin-2-yl)piperidin-4-ylamino] benzoic acid tert-butyl ester (17). 4-amino-2-chloro-quinazoline (0.070 g, 0.39 mmol) was added to a solution of (49) (0.13 g, 0.47 mmol) in n-pentanol (5 mL) at 25° C. The mixture was heated to 120° C. and was maintained at that temperature for 12 h. The reaction mixture was then cooled to room temperature and concentrated to a brown yellow oily residue. Purification of the residue by flash column chromatography (gradient elution 0 to 5% MeOH in $CH_2Cl_2$) provided the title compound (0.12 g, 73%): TLC ($R_f$=0.33; 5% MeOH/$CH_2Cl_2$); $^1$H NMR ($CDCl_3$) δ 7.83 (d, 2H, J=8.7), 7.51 (m, 3H), 7.10 (t, 1H, J=6.6), 6.57 (d, 2H, J=8.8), 5.35 (br s, 2H), 4.81 (d, 2H, J=13.6), 4.00 (br s, 1H), 3.60 (m, 1H), 3.14 (t, 2H, J=14.0), 2.13 (d, 2H, J=13.2), 1.57 (s, 9H), 1.47 (m, 2H); $^{13}$C NMR ($CDCl_3$) δ 166.1, 161.6, 158.8, 152.0, 150.4, 133.2, 131.5, 125.9, 121.8, 121.3, 120.3, 111.8, 109.7, 79.9, 50.3, 42.8, 32.3, 28.3; Anal. ($C_{24}H_{29}N_5O_2 \cdot 1/4HCl$)·C, H, N.

Example 12

3-Amino-5-[1-(4-amino-6,7-dimethoxyquinazolin-2-yl)piperidin-4-ylamino]-6-chloropyrazine-2-carboxylic acid (18)

3-Amino-5-[1-(4-amino-6,7-dimethoxyquinazolin-2-yl)piperidin-4-ylamino]-6-chloropyrazine-2-carboxylic acid (18). Potassium hydroxide (0.26 g, 4.7 mmol) was added to a solution of (1) (0.06 g, 0.123 mmol) in ethanol (2 mL) at 25° C. The reaction mixture was heated at 85° C. for 12 h then cooled to room temperature. The mixture was concentrated, acidified with HCl (aq) (2 mL, 3M) and the desired product was filtered and rinsed with cold $H_2O$ to give 0.05 g (89%) of the title compound: $^1$H NMR (DMSO) δ 12.20 (br s, 1H), 8.50 (br s, 1H), 7.69 (s, 1H), 7.40 & 7.31 (br s, 2H), 7.16 (d, 1H, J=7.2), 4.70 (d, 2H, J=11.5), 4.24 (m, 1H), 3.86 (s, 3H), 3.82 (s, 3H), 3.10 (m, 2H), 1.92 (m, 2H), 1.66 (m, 2H); $^{13}$C NMR (DMSO) δ 167.4, 161.3, 155.7, 155.1, 150.6, 146.5, 119.0, 109.2, 104.8, 101.7, 56.2, 55.9, 47.7, 43.9, 30.4; HRMS (FAB) m/z 475.1589 (M+H)$^+$ ($C_{20}H_{23}N_8O_4Cl$ requires 475.1604); Anal. ($C_{20}H_{23}N_8O_4Cl \cdot 2HCl \cdot 1/2H_2O$) C, H, N.

Example 13

3-Amino-5-[1-(4-amino-6,7-dimethoxyquinazolin-2-yl)piperidin-4-ylamino]pyrazine-2-carboxylic acid (19)

3-Amino-5-[1-(4-amino-6,7-dimethoxyquinazolin-2-yl)piperidin-4-ylamino]pyrazine-2-carboxylic acid (19). Potassium hydroxide (0.53 g, 9.46 mmol) was added to a solution of (2) (0.23 g, 0.47 mmol) in MeOH/$H_2O$ (20 mL, 10%; v/v) at 25° C. The reaction mixture was heated at 85° C. for 12 h then cooled to room temperature. The mixture was concentrated, acidified with HCl (aq) (20 mL, 3M) and the desired product was filtered and rinsed with cold $H_2O$ to give 0.21 g (93%) of the title compound: $^1$H NMR (DMSO) δ 12.45 (br s, 1H), 8.78 (br, 2H), 8.37 (s, 1H), 7.78 (s, 1H), 7.68 (s, 1H), 7.38 (s, 1H), 5.19 (br s, 3H), 4.56 (m, 2H), 4.13 (m, 1H), 3.85 (s, 3H), 3.83 (s, 3H), 3.41 (m, 2H), 2.04 (m, 2H), 1.54 (m, 2H); $^{13}$C NMR (DMSO) δ 167.0, 161.3, 155.8, 155.1, 154.4, 151.0, 146.7, 136.3, 121.3, 121.0, 105.2, 101.6, 99.3, 56.3, 56.0, 46.5, 43.3, 30.5; HRMS (FAB) m/z 441.1988 (M+H)$^+$ ($C_{20}H_{24}N_8O_4$ requires 441.1999).

Example 14

6-[1-(4-Amino-6,7-dimethoxyquinazolin-2-yl)piperidin-4-ylamino]nicotinic acid (20)

6-[1-(4-Amino-6,7-dimethoxyquinazolin-2-yl)piperidin-4-ylamino]nicotinic acid (20). Potassium hydroxide (1.18 g, 21.1 mmol) was added to a solution of (3) (0.5 g, 1.05 mmol) in MeOH/$H_2O$ (20 mL, 10%; v/v). The reaction mixture was heated to 85° C. for 12 h, then cooled to room temperature. The mixture was concentrated, acidified with HCl (aq) (20 mL, 3M) and the desired product was filtered and rinsed with cold $H_2O$ to give 0.46 g (quantitative yield) of the title compound: $^1$H NMR (DMSO) δ 12.36 (br s, 1H), 9.56 (br s, 1H), 8.78 (br s, 2H), 8.36 (s, 1H), 8.07 (d, 1H, J=9.2), 7.75 (s, 1H), 7.61 (s, 1H), 7.11 (d, 1H, J=9.3), 4.64 (m, 2H), 4.29 (m, 1H), 3.85 (s, 3H), 3.83 (s, 3H), 3.37 (m, 2H), 2.12 (m, 2H), 1.60 (m, 2H); $^{13}$C NMR (DMSO) δ 164.7, 161.3, 155.2, 154.4, 151.0, 146.7, 141.8, 140.1, 136.3, 115.2, 112.4, 105.2, 101.6, 99.3, 56.3, 56.0, 48.4, 43.3, 30.4; HRMS (FAB) m/z 425.1948 (M+H)$^+$ ($C_{21}H_{24}N_6O_4$ requires 425.1937); Anal. ($C_{21}H_{24}N_6O_4 \cdot 2HCl \cdot 2H_2O$) C, H, N.

Example 15

4-[1-(4-Amino-6,7-dimethoxyquinazolin-2-yl)piperidin-4-ylamino]-3-nitrobenzoic acid (21)

4-[1-(4-Amino-6,7-dimethoxyquinazolin-2-yl)piperidin-4-ylamino]-3-nitrobenzoic acid (21). A solution of (6) (0.03 g, 0.057 mmol) in TFA (5 mL) was capped with a drying tube and stirred at 25° C. for 12 h. The reaction mixture was evaporated to a pale yellow solid residue (0.026 g, 78 %); $^1$H NMR (DMSO) δ 11.75 (br s, 1H), 8.81 (s, 1H), 8.69 (s, 1H), 8.61 (d, 1H, J=1.9), 8.24 (d, 1H, J=7.7), 7.99 (d, 1H, J=7.3), 7.67 (s, 1H), 7.34 (d, 1H, J=9.3), 7.20 (s, 1H), 4.49 (d, 2H, J=13.2), 4.11 (m, 1H), 3.89 (s, 3H), 3.83 (s, 3H), 3.37 (t, 2H, J=11.8), 2.12 (d, 2H, J=10.3), 1.76 (m, 2H); $^{13}$C NMR (DMSO) δ 165.8, 161.4, 157.8, 155.4, 151.2, 146.8, 146.2, 136.1, 130.6, 128.6, 117.5, 115.0, 104.8, 101.6, 98.8, 56.1, 56.0, 48.8, 43.3, 30.4; HRMS (FAB) m/z 469.1816 (M+H)$^+$ ($C_{22}H_{24}N_6O_6$ requires 469.1830); Anal. ($C_{22}H_{24}N_6O_6 \cdot 11/2CF_3COOH \cdot 11/4H_2O \cdot 1/4CH_3OH$) C, H, N.

Example 16

4-[1-(6,7-Dimethoxyquinazolin-2-yl)piperidin-4-ylamino]benzoic acid (28)

4-[1-(6,7-Dimethoxyquinazolin-2-yl)piperidin-4-ylamino]benzoic acid (28). A solution of (13) (0.014 g, 0.029 mmol) in trifluoroacetic acid (3 mL) was capped with a drying tube and stirred at 25° C. for 12 h. The reaction mixture was evaporated to a yellow solid residue (0.020 g, quantitative yield); $^1$H NMR (DMSO) δ 8.95 (s, 1H), 7.66 (d, 2H, J=8.7), 7.23 (s, 1H), 6.94 (s, 1H), 6.62 (d, 2H, J=8.8), 4.67 (d, 2H, J=13.6), 3.90 (s, 3H), 3.83 (s, 3H), 3.64 (m, 1H), 3.19 (t, 2H, J=11.5), 2.00 (d, 2H, J=12.8), 1.38 (m, 2H); $^{13}$C NMR (DMSO) δ 167.5, 157.9, 156.3, 151.6, 146.6, 131.2, 129.6, 123.9, 116.7, 113.8, 111.2, 105.6, 104.0, 55.9, 55.6, 48.8, 42.7, 31.2; HRMS (FAB) m/z 409.1878 (M+H)$^+$ ($C_{22}H_{24}N_4O_4$ requires 409.1876); Anal. ($C_{22}H_{24}N_4O_4 \cdot 3CF_3COOH \cdot 11/4H_2O \cdot 1CH_3OH$) C, H, N.

Example 17

4-[1-(4,6,7-Trimethoxyquinazolin-2-yl)piperidin-4-ylamino]benzoic acid (29)

4-[1-(4,6,7-Trimethoxyquinazolin-2-yl)piperidin-4-ylamino]benzoic acid (29). A solution of (14) (0.062 g, 0.13 mmol) in trifluoroacetic acid (3 mL) was capped with a drying tube and stirred at 25° C. for 12 h. The reaction mixture was evaporated to a light brown oily residue (0.08 g, quantitative yield); $^1$H NMR (DMSO) δ 7.68 (d, 2H, J=8.7), 7.25 (s, 1H), 7.23 (s, 1H), 6.66 (d, 2H, J=8.7), 4.54 (d, 2H, J=12.0), 4.15 (s, 3H), 3.91 (s, 3H), 3.85 (s, 3H), 3.73 (m, 1H), 3.45 (t, 2H, J=12.0), 2.10 (m, 2H), 1.53 (m, 2H): $^{13}$C NMR (DMSO) δ 167.5, 156.5, 151.4, 149.7, 148.9, 147.1, 131.2, 117.0, 111.2, 106.1, 103.0, 102.8, 101.1, 56.2, 55.9, 55.3, 47.9, 43.7, 30.9; HRMS (FAB) m/z 439.2001 (M+H)$^+$ (C$_{23}$H$_{26}$N$_4$O$_5$ requires 439.1981); Anal. (C$_{23}$H$_{26}$N$_4$O$_5$·1CF$_3$COOH·1/2H$_2$O) C, H, N.

Example 18

4-[1-(6,7-Dimethoxy-4-oxo-3,4-dihydroquinazolin-2-yl)piperidin-4-ylamino]benzoic acid (30)

4-[1-(6,7-Dimethoxy-4-oxo-3,4-dihydroquinazolin-2-yl) piperidin-4-ylamino]benzoic acid (30). A solution of (15) (0.036 g, 0.074 mmol) in trifluoroacetic acid (5 mL) was capped with a drying tube and stirred at 25° C. for 12 h. The reaction mixture was evaporated to a light brown oily residue (0.059 g, quantitative yield); $^1$H NMR (DMSO) δ 8.00 (br s, 1H), 7.67 (d, 2H, J=8.3), 7.31 (s, 1H), 6.98 (s, 1H), 6.63 (d, 2H, J=8.2), 6.12 (br s, 1H), 4.22 (d, 2H, J=12.8), 3.86 (s, 3H), 3.81 (s, 3H), 3.65 (m, 1H), 3.28 (m, 2H), 2.03 (m, 2H), 1.49 (m, 2H); $^{13}$C NMR (DMSO) δ 167.5, 161.8, 160.7, 155.2, 151.4, 149.6, 146.3, 131.2, 124.2, 123.9, 116.9, 111.2, 108.2, 105.8, 55.8, 55.7, 47.9, 44.6, 30.8; HRMS (FAB) m/z 425.1818 (M+H)$^+$ (C$_{22}$H$_{24}$N$_4$O$_5$ requires 425.1819); Anal. (C$_{22}$H$_{24}$N$_4$O$_5$·2CF3COOH·1CH$_3$OH) C, H, N.

Example 19

4-[1-(6,7-Dimethoxy-4-p-tolylaminoquinazolin-2-yl) piperidin-4-ylamino]benzoic acid (31)

4-[1-(6,7-Dimethoxy-4-p-tolylaminoquinazolin-2-yl) piperidin-4-ylamino]benzoic acid (31). A solution of (16) (0.040 g, 0.07 mmol) in trifluoroacetic acid (5 mL) was capped with a drying tube and stirred at 25° C. for 12 h. The reaction mixture was evaporated to a light brown solid residue (0.05 g, quantitative yield); $^1$H NMR (DMSO) δ 12.10 (br s, 1H), 10.56 (br s, 1H), 7.92 (s, 1H) 7.67 (d, 2H, J=8.5), 7.51 (d, 2H, J=8.3), 7.27 (s, 1H), 7.26 (d, 2H, J=7.9), 6.64 (d, 2H, J=8.4), 4.32 (d, 2H, J=12.6), 3.91 (s, 3H), 3.89 (s, 3H), 3.68 (m, 1H), 3.36 (t, 2H, J=10.7), 2.32 (s, 3H), 2.05 (d, 2H, J=8.0), 1.47 (m, 2H); $^{13}$C NMR (DMSO) δ 167.4, 157.2, 155.4, 151.4, 150.7, 147.0, 136.4, 135.0, 134.6, 131.2, 129.1, 124.0, 117.0, 111.2, 104.3, 102.2, 99.1, 56.3, 56.1, 47.9, 43.5, 30.8, 20.6; HRMS (FAB) m/z 514.2459 M+H)$^+$ (C$_{29}$H$_{31}$N$_5$O$_4$ requires 514.2454); Anal. (C$_{29}$H$_{31}$N$_5$O$_4$·1CF$_3$COOH·11/4H$_2$O) C, H, N.

Example 20

4-[1-(4-Aminoquinazolin-2-yl)piperidin-4-ylamino] benzoic acid (32)

4-[1-(4-Aminoquinazolin-2-yl)piperidin-4-ylamino] benzoic acid (32). A solution of (17) (0.058 g, 0.14 mmol) in trifluoroacetic acid (2 mL) was capped with a drying tube and stirred at 25° C. for 12 h. The reaction mixture was evaporated to a light brown oily residue (0.077 g, quantitative yield); $^1$H NMR (DMSO) δ 11.8 (br s, 1H), 9.07 & 8.95 (br s, 2H), 8.20 (d, 1H, J=7.8), 7.82 (t, 1H, J=7.8), 7.68 (d, 3H, J=8.5), 7.42 (t, 1H, J=7.4), 6.65 (d, 2H, J=8.8), 4.47 (d, 2H, J=13.2), 3.73 (m, 1H), 3.42 (t, 2H, J=11.3), 2.07 (d, 2H, J=10.7), 1.50 (m, 2H); $^{13}$C NMR (DMSO) δ 167.4, 162.1, 151.4, 139.8, 135.4, 131.2, 124.6, 120.0, 117.3, 117.0, 111.2, 109.1, 47.8, 43.4, 30.9. Anal. (C$_{20}$H$_{21}$N$_5$O$_2$·11/2CF$_3$COOH) C, H, N.

Example 21

3-Amino-5-[N'-(4-amino-6,7-dimethoxy-quinazolin-2-yl)-hydrazino]-6-chloro-pyrazine-2-carboxylic acid methyl ester (7)

3-Amino-6-chloro-5-hydrazino-pyrazine-2-carboxylic acid methyl ester (51). Methyl 3-amino-5,6-dichloro-2-pyrazinecarboxylate (1.10 g, 5 mmol) was dissolved in 20 mL of tert-butyl alcohol and DMF (v/v; 1:1). Anhydrous hydrazine (0.18 mL, 5.5 mmol) and N,N'-diisopropylethyl amine (4.5 mL, 25 mmol) were then added sequentially at 25° C. The resulting mixture was stirred at 25° C. for 12 h. The reaction mixture was then partitioned between EtOAc (100 mL) and sat. NaCl (aq) (100 mL). The organic layer was dried (Na$_2$SO$_4$), filtered, and concentrated in vacuo to give a brown solid residue. This residue was used in the next-step reaction without further purification: TLC (R$_f$= 0.53; 10% MeOH/CH$_2$Cl$_2$).

3-Amino-5-[N'-(4-amino-6,7-dimethoxy-quinazolin-2-yl)-hydrazino]-6-chloro-pyrazine-2-carboxylic acid methyl ester (7). Compound (51) (5 mmol) was added to a solution of 4-amino-2-chloro-6,7-dimethoxy quinazoline (0.96 g, 4 mmol) in isoamyl alcohol (10 mL) at 25° C. The mixture was then stirred at 120° C. for 12 h. After cooling to room temperature, the desired product was filtered and rinsed with acetone to give 1.62 g (96%) of the title compound: TLC (R$_f$=0.30; 10% CH$_3$OH/CH$_2$Cl$_2$); $^1$H NMR (DMSO) δ 11.90 (br, 1H), 10.30 (br, 1H), 9.80 (br, 1H), 9.00 (br, 1H), 8.80 (br, 1H), 7.80 (s, 1H), 7.69 (d, 1H, J=2.0), 7.41 (s, 1H), 7.19 (s, 1H), 3.86 (s, 3H), 3.85 (s, 3H), 3.76 (s, 3H); HRMS (FAB) m/z 421.1152 (M+H)$^+$ (C$_{16}$H$_{18}$N$_8$O$_4$Cl requires 421.1110); Anal. (C$_{16}$H$_{18}$N$_8$O$_4$Cl·1/4CH$_3$OH) C, H, N.

Example 22

4-(1-Naphthalen-2-yl-piperidin-4-ylamino)-benzoic acid tert-butyl ester (8)

4-(1-Naphthalen-2-yl-piperidin-4-ylamino)-benzoic acid tert-butyl ester (8). Sodium tert-butoxide (0.4 g, 4 mmol) was added to a solution of 2-bromonaphthalene (0.3 g, 1.48 mmol) and 49 (0.4 g, 1.48 mmol) in 5 mL of anhydrous toluene at 25° C. Tris(dibenzylideneacetone)-dipalladium (0) (6 mg, 0.007 mmol) and (+)-2,2'-bis (diphenylphosphino)-1,1'-binaphthyl [(±)-BINAP] (12.4 mg, 0.02 mmol) were added sequentially. The reaction mixture was heated to 80° C. and maintained at that temperature for 12 h, then was cooled to 25° C. and diluted with a mixture of CH$_3$OH/CH$_2$Cl$_2$ (150 mL, v/v, 50:50). The diluted mixture was filtered through celite and the filtrate was concentrated in vacuo. The resulting residue was partitioned between CH$_2$Cl$_2$ (150 mL) and H$_2$O (150 mL). The organic layer was dried (Na$_2$SO$_4$), filtered, and concentrated in vacuo to give a deep yellow solid residue. Purification of the residue by flash column chromatography (gradient elution 0 to 25% EtOAc in hexanes) provided the title compound (0.35 g, 59%): TLC (R$_f$=0.80; 40% EtOAc/hexanes); $^1$H NMR (CDCl$_3$) δ 7.83 (d, 2H, J=8.4), 7.70 (m, 3H), 7.32 (m, 3H), 7.15 (d, 1H, J=2.1), 6.56 (d, 2H, J=8.7), 4.02 (d, 1H, J=7.8), 3.76 (d, 2H, J=12.7), 3.54 (m, 1H), 2.98 (t, 2H, J=12.0), 2.20 (d, 2H, J=10.7), 1.67 (m, 2H), 1.57 (s, 9H); $^{13}$C NMR (CDCl$_3$) δ 166.0, 150.4, 149.1, 134.7, 131.5, 128.7, 128.5, 127.4, 126.7, 126.3, 123.4, 120.6, 119.8, 111.9, 110.7, 79.8, 49.6, 48.8, 32.1, 28.4; HRMS (FAB) m/z 402.2321 (M)$^+$ (C$_{26}$H$_{30}$N$_2$O$_2$ requires 402.2307).

Example 23

4-(1-Naphthalen-2-ylpiperidin-4-ylamino)benzoic acid (23)

4-(1-Naphthalen-2-ylpiperidin-4-ylamino)benzoic acid (23). A solution of (8) (0.067 g, 0.17 mmol) in HCl (10 mL, 4M in 1,4-dioxane) was capped with a drying tube and stirred at 25° C. for 12 h. The reaction mixture was concentrated to give a white solid residue (0.065 g, 99%); $^1$H NMR (DMSO) δ 8.31 (s, 1H), 8.06 (m, 5H), 7.70 (d, 2H, J=8.7), 7.60 (m, 2H), 6.70 (d, 2H, J=8.8), 3.76 (m, 5H), 2.17 (m, 4H); $^{13}$C NMR (DMSO) δ 167.4, 151.2, 132.7, 131.2, 129.9, 128.0, 127.8, 127.4, 119.3, 117.4, 111.4, 66.3, 29.0; HRMS (FAB) m/z 347.1770 (M+H)$^+$ ($C_{22}H_{22}N_2O_2$ requires 347.1760); Anal. ($C_{22}H_{22}N_2O_2$·2HCl) C, H, N.

Example 24

4-[1-(Naphthalene-2-carbonyl)-piperidin-4-ylamino]-benzoic acid tert-butyl ester (10)

4-[1-(Naphthalene-2-carbonyl)-piperidin-4-ylamino] benzoic acid tert-butyl ester (10). Compound (49) (0.056 g, 0.2 mmol) and triethylamine (0.14 mL, 1 mmol) were added sequentially to a solution of 2-naphthoyl chloride (0.114 g, 0.6 mmol) in $CH_2Cl_2$ (5 mL) at 25° C. The mixture was stirred at 25° C. for 12 h, then was concentrated in vacuo to a residue. Purification of the residue by flash column chromatography (gradient elution 5 to 30% EtOAc in hexanes) provided the title compound (0.04 g, 50%): TLC ($R_f$=0.50; 50% EtOAc/hexanes); $^1$H NMR (CDCl$_3$) δ 7.84 (m, 6H), 7.51 (m, 3H), 6.55 (d, 2H, J=8.8), 4.65 (br s, 1H), 4.01 (d, 2H, J=7.8), 3.66 (m, 1H), 3.18 (t, 2H, J=11.2), 2.05 (m, 2H), 1.56 (s, 9H), 1.46 (m, 2H); $^{13}$C NMR (CDCl$_3$) δ 170.5, 166.0, 150.1, 133.8, 133.3, 132.9, 131.5, 128.4, 127.9, 127.8, 127.1, 126.8, 124.2, 121.1, 111.9, 79.9, 49.9, 32.6, 28.4; HRMS (FAB) m/z 430.2241 (M)$^+$ ($C_{27}H_{30}N_2O_3$ requires 430.2256).

Example 25

4-[1-(Naphthalene-2-carbonyl)piperidin-4-ylamino] benzoic acid (25)

4-[1-(Naphthalene-2-carbonyl)piperidin-4-ylamino] benzoic acid (25). A solution of (10) (0.039 g, 0.09 mmol) in HCl (5 mL, 4M in 1,4-dioxane) was capped with a drying tube and stirred at 25° C. for 12 h. The reaction mixture was concentrated to give a white solid residue (0.02 g, 57%); $^1$H NMR (DMSO) δ 7.98 (m, 4H), 7.66 (d, 2H, J=8.7), 7.55 (m, 3H), 6.65 (d, 2H, J=8.8), 4.41 (m, 2H), 3.67 (m, 1H), 3.15 (m, 2H), 1.95 (m, 2H), 1.40 (m, 2H); $^{13}$C NMR (DMSO) δ 169.0, 167.4, 151.1, 133.6, 133.1, 132.3, 131.1, 128.3, 128.1, 127.7, 127.1, 126.8, 126.1, 124.3, 117.3, 111.6, 48.7, 45.9, 31.2; HRMS (FAB) m/z 375.1693 (M+H)$^+$ ($C_{23}H_{22}N_2O_3$ requires 375.1709); Anal. ($C_{23}H_{22}N_2O_3$·2HCl·4H$_2$O) C, H, N.

Example 26

4-[1-(Naphthalene-2-sulfonyl)-piperidin-4-ylamino] benzoic acid tert-butyl ester (9)

4-[1-(Naphthalene-2-sulfonyl)-piperidin-4-ylamino]-benzoic acid tert-butyl ester (9). Compound (49) (0.056 g, 0.2 mmol) and triethylamine (0.14 mL, 1 mmol) were added sequentially to a solution of 2-naphthalene sulfonyl chloride (0.136 g, 0.6 mmol) in $CH_2Cl_2$ (5 mL) at 25° C. The mixture was stirred at 25° C. for 12 h then was concentrated under reduced pressure. Purification of the residue by flash column chromatography (gradient elution 0 to 30% EtOAc in hexanes) provided the title compound (0.09 g, 92.5%): TLC ($R_f$=0.50; 40% EtOAc/Hexanes); $^1$H NMR (CDCl$_3$) δ 8.35 (s, 1H), 7.98 (m, 3H) 7.73 (m, 5H), 6.43 (d, 2H, J=8.7), 3.86 (d, 2H, J=9.2), 3.78 (s, 1H), 3.60 (m, 1H), 2.60 (t, 2H, J=10.5), 2.11 (d, 2H, J=13.4), 1.60 (m, 2H), 1.54 (s, 9H); $^{13}$C NMR (CDCl$_3$) δ 165.9, 149.9, 135.0, 133.2, 132.2, 131.4, 129.3, 129.2, 129.0, 128.9, 128.0, 127.7, 123.0, 121.1, 111.9, 79.9, 49.0, 45.2, 31.7, 28.4; HRMS (FAB) m/z 467.2019 (M+H)$^+$ ($C_{26}H_{30}N_2O_4S$ requires 467.2005).

Example 27

4-[1-(Naphthalene-2-sulfonyl)piperidin-4-ylamino] benzoic acid (24)

4-[1-(Naphthalene-2-sulfonyl)piperidin-4-ylamino] benzoic acid (24). A solution of (9) (0.05 g, 0.12 mmol) in HCl (2 mL, 4M in 1,4-dioxane) was capped with a drying tube and stirred at 25° C. for 12 h. The reaction mixture was then concentrated to give a pale yellow oily residue (0.03 g, 68%); $^1$H NMR (DMSO) δ 8.44 (s, 1H), 8.20 (m, 1H), 8.09 (m, 1H), 7.72 (m, 4H), 7.57 (d, 2H, J=5.7), 6.50 (d, 2H, J=6.8), 3.60 (m, 2H), 3.25 (m, 1H), 2.55 (m, 2H), 1.93 (d, 2H, J=11.9), 1.45 (m, 2H); $^{13}$C NMR (DMSO) δ 167.4, 151.3, 134.4, 132.7, 131.9, 131.1, 129.3, 129.0, 128.6, 127.9, 122.9, 111.2, 47.2, 45.0, 30.6; HRMS (FAB) m/z 411.1366 (M+H)$^+$ ($C_{22}H_{22}N_2O_4S$ requires 411.1379); Anal. ($C_{22}H_{22}N_2O_4S$·2HCl·2H$_2$O) C, H, N.

Example 28

4-[1-(5-Methoxy-1H-benzoimidazol-2-yl)piperidin-4-ylamino]benzoic acid tert-butyl ester (12)

4-[1-(5-Methoxy-1H-benzoimidazol-2-yl)piperidin-4-ylamino]benzoic acid tert-butyl ester (12). 2-Chloro-5-methoxybenzimidazole (0.089 g, 0.49 mmol) was added to a solution of (49) (0.14 g, 0.5 mmol) in n-pentanol (3 mL) at 25° C. The mixture was heated to 120° C. and was maintained at that temperature for 12 h. The reaction mixture was cooled to room temperature and the desired product was filtered and rinsed with acetone to give 0.17 g (83.3%) of the title compound: TLC ($R_f$=0.30; 5% MeOH/CH$_2$Cl$_2$); $^1$H NMR (DMSO) δ 13.40 (br s, 1H), 7.63 (d, 2H, J=8.3), 7.29 (d, 1H, J=8.7), 6.91 (s, 1H), 6.83 (d, 1H, J=8.4), 6.65 (d, 2H, J=8.3), 6.50 (s, 1H), 4.13 (d, 2H, J=12.7), 3.77 (s, 3H), 3.73 (m, 1H), 3.47 (m, 4H), 2.06 (d, 2H, J=11.0), 1.48 (s, 9H); $^{13}$C NMR (DMSO) δ 165.2, 156.1, 151.3, 149.8, 131.0, 130.9, 124.0, 117.8, 111.8, 111.3, 110.2, 96.4, 79.0, 55.7, 47.3, 45.6, 30.2, 30.0; HRMS (FAB) m/z 423.2388 (M+H)$^+$ ($C_{24}H_{30}N_4O_3$ requires 423.2389); Anal. ($C_{24}H_{30}N_4O_3$·1HCl·1/2H$_2$O) C, H, N.

Example 29

4-[1-(5-Methoxy-1H-benzoimidazol-2-yl)piperidin-4-ylamino]benzoic acid (27)

4-[1-(5-Methoxy-1H-benzoimidazol-2-yl)piperidin-4-ylamino]benzoic acid (27). A solution of (12) (0.03 g, 0.071 mmol) in TFA (5 mL) was capped with a drying tube and stirred at 25° C. for 12 h. The reaction mixture was then concentrated to a light brown oily residue (0.033 g, 97.5%); $^1$H NMR (DMSO) δ 13.00 (br s, 1H), 7.68 (d, 2H, J=8.6), 7.30 (d, 1H, J=8.7), 6.92 (d, 1H, J=2.2), 6.85 (dd, 1H, J=8.0, 2.3), 3.99 (d, 2H, J=13.3), 3.78 (s, 3H), 3.70 (m, 1H), 3.46 (t, 2H, J=11.2), 2.09 (d, 2H, J=10.7), 1.56 (m, 2H); $^{13}$C NMR (DMSO) δ 167.4, 156.2, 151.3, 150.0, 131.2, 131.0, 124.0, 117.1, 111.9, 111.3, 110.3, 96.6, 55.7, 47.3, 45.4, 30.2; HRMS (FAB) m/z 367.1777 (M+H)$^+$ ($C_{20}H_{22}N_4O_3$ requires 367.1765); Anal. ($C_{20}H_{22}N_4O_3$·1CF$_3$COOH·3/4H$_2$O) C, H, N.

Example 30

4-(1-Pyrimidin-2-ylpiperidin-4-ylamino)benzoic acid tert-butyl ester (11)

4-(1-Pyrimidin-2-ylpiperidin-4-ylamino)benzoic acid tert-butyl ester (11). 2-Bromopyrimidine (0.016 g, 0.1 mmol) was added to a solution of (49) (0.032 g, 0.12 mmol) in tert-butyl alcohol (2 mL) at 25° C. The mixture was heated to 90° C. and was maintained at that temperature for 12 h. The reaction mixture was then cooled to room temperature and concentrated to a yellow oily residue. Purification of the residue by flash column chromatography (gradient elution 0 to 20% EtOAc in hexanes) provided the title compound (0.032 g, 89%): TLC ($R_f$=0.41; 40% EtOAc/hexanes); $^1$H NMR (CDCl$_3$) δ 8.29 (d, 2H, J=4.7), 7.80 (d, 2H, J=8.8), 6.54 (d, 2H, J=8.8), 6.46 (t, 1H, J=4.7), 4.66 (d, 2H, J=13.7), 3.96 (d, 1H, J=7.8), 3.63 (m, 1H), 3.13 (t, 2H, J=12.0), 2.12 (d, 2H, J=12.0), 1.54 (s, 9H), 1.43 (m, 2H); $^{13}$C NMR (CDCl$_3$) δ 166.1, 161.6, 157.8, 150.3, 131.5, 120.5, 111.8, 109.8, 79.9, 50.1, 42.6, 32.1, 28.3; HRMS (FAB) m/z 355.2126 (M+H)$^+$ (C$_{20}$H$_{26}$N$_4$O$_2$ requires 355.2134).

Example 31

4-(1-Pyrimidin-2-ylpiperidin-4-ylamino)benzoic acid (26)

4-(1-Pyrimidin-2-ylpiperidin-4-ylamino)benzoic acid (26). A solution of (11) (0.009 g, 0.025 mmol) in HCl (5 mL, 4M in 1,4-dioxane) was capped with a drying tube and stirred at 25° C. for 12 h. The reaction mixture was evaporated to a pale yellow oily residue (0.009 g, quantitative yield); $^1$H NMR (DMSO) δ 8.42 (d, 2H, J=4.8), 7.67 (d, 2H, J=8.7), 6.70 (t, 1H, J=4.8), 6.67 (d, 2H, J=9.3), 4.54 (d, 2H, J=13.2), 3.72 (m, 1H), 3.20 (t, 2H, J=11.1), 1.98 (d, 2H, J=10.7), 1.34 (m, 2H); $^{13}$C NMR (CDCl$_3$) δ 167.4, 158.9, 157.7, 151.0, 131.2, 117.4, 111.7, 109.7, 48.9, 43.6, 30.9; HRMS (FAB) m/z 299.1518 (M+H)$^+$ (C$_{16}$H$_{18}$N$_4$O$_2$ requires 299.1508).

Example 32

2-Chloro-6,7-dimethoxyquinazoline (QH)

2-Chloro-6,7-dimethoxyquinazoline (QH). Sodium borohydride (0.23 g, 6.1 mmole) was added to a solution of 2,4-dichloro-6,7-dimethoxyquinazoline (1.0 g, 4 mmol) in EtOH/CH$_2$Cl$_2$ (40 mL; 1:1; v/v) at 25° C. The mixture was stirred at 25° C. for 12 h then was poured into cold HCl aqueous solution (0.4 M, 200 mL). The resulting mixture was basicified with saturated NaHCO$_3$ (aq) and then extracted with EtOAc (3×100 mL). The combined organic layers were dried (Na$_2$SO$_4$), filtered, and concentrated in vacuo to give a yellowish white solid reside. Purification of the residue by flash column chromatography (gradient elution 20 to 35% EtOAc/hexanes) provided the title compound (0.33 g, 37%): TLC ($R_f$=0.50; 50% EtOAc/hexanes); $^1$H NMR (DMSO) δ 9.25 (s, 1H), 7.55 (s, 1H), 7.36 (s, 1H), 3.98 (s, 3H), 3.93 (s, 3H); $^3$C NMR (CDCl$_3$) δ 159.1, 157.3, 156.1, 150.9, 150.1, 119.4, 105.9, 103.7, 56.6, 56.4; HRMS (FAB) m/z 225.0431 (M+H)$^+$ (C$_{10}$H$_9$N$_2$O$_2$Cl requires 225.0431); Anal. (C$_{10}$H$_9$N$_2$O$_2$Cl·3/4H$_2$O·1/4CH$_3$OH) C, H, N.

Example 33

3-amino-5-{4-(4-t-boc-piperazinyl-6,7-dimethoxy-2-quinazolinyl)-1-piperazinyl}-6-chloro-2-pyrazine carboxylic acid, methyl ester (52)

2-chloro-4-t-boc-piperazinyl-6,7-dimethoxy-quinazoline. A solution of 2,4-dichloro-6,7-dimethoxy-quinazoline (10.3 g, 40 mmol) in dry THF (500 mL) was treated with Hunig's base (10 mL) and t-Boc-piperazine (10 g, 54 mmol) at room temp. for 16 hrs. The ppt. was filtered off and conc. in vacuo. The resultant solid was chromatographed on silica gel CH$_2$Cl$_2$/EtOAc to afford the product. m.p. 155–157, $^1$H NMR CDCl$_3$ 1.54 (s, 9H, t-Boc), 3.7 (m, 8H, piperazine), 4.05 (s, 6H, OCH$_3$), 7.0 (s, 1H, ArH), 7.2 (s, 1H, ArH)

2-piperazinyl-4-t-boc-piperazinyl-6,7-dimethoxy-quinazoline. A solution of 2-chloro-4-t-boc-piperazinyl-6,7-dimethoxy-quinazoline (10.1 g, 25 mmol) CH$_3$CN (500 ml.), and piperazine (19 g, 220 mmol) was heated at reflux for 16 hours. The ppt. was filtered off and conc. in vacuo and chromatographed on silica gel EtOAc/MeOH to afford the product. m.p. 127–130 $^1$H NMR DMSO 1.4 (s, 9H, t-boc), 2.92 (m, 4H, piperazinyl), 3.53 (m, 8H, piperazinyl), 3.87 (m, 10H, piperazinyl, OCH$_3$), 6.87 (s, 1H, Ar), 7.0 (s, 1H, Ar)

3-amino-5-{4-(4-t-boc-piperazinyl-6,7-dimethoxy-2-quinazolinyl)-1-piperazinyl}-6-chloro-2-pyrazine carboxylic acid, methyl ester (52). A solution of 2-piprazinyl-4-t-boc-piperazinyl-6,7-dimethoxy-quinazoline (2.3 g, 5 mmol), isoamyl alcohol (200 mL) Hunig's base (5 mL) methyl-3-amino-5,6-dichloro-2-pyrazinecarboxylate (1.1 g, 5 mmol) was heated at 80° C. for 16 hrs. The cooled reaction was filtered and conc. in vacuo. Trituration with ether afforded the product. See FIG. 1. $^1$H NMR DMSO 1.45 (s, 9H, t-boc), 3.2–3.34 (m, 25H, piperazinyl, OCH$_3$, CO$_2$Me), 6.89 (s, 1h, Ar), 7.0 (s,1H, Ar) m.w. 644.13, m.s. +645

Example 34

3-amino-5-{4-(4-piperazinyl-6,7-dimethoxy-2-quinazolinyl)-1-piperazinyl}-N-(aminoiminomethyl-6-chloro-2-pyrazinecarboxamide (54)

3-amino-5-{4-(4-t-boc-piperazinyl-6,7-dimethoxy-2-quinazolinyl)-1-piperazinyl}-N-(aminoiminomethyl)-6-chloro-2-pyrazinecarboxamide (53). A solution of 3-amino-5-{4-(4-t-boc-piperazinyl-6,7-dimethoxy-2-quinazolinyl)-1-piperazinyl}-6-chloro-2-pyrazine carboxylic acid, methyl ester (52) (1.5 g, 2.3 mmol) in DMF (100 mL) was treated with 1 equiv. of freshly generated guanidine. The reaction was heated at 75° C. for 8 hrs. Upon cooling the reaction was filtered and conc. in vacuo. Chromatography on silica gel EtOAc/MeOH afforded the product as a solid. $^1$H NMR DMSO 1.44 (s, 9H, t-boc), 3.3–3.97 (m, 22H, piperazinyl, OCH$_3$), 6.89 (s, 1H, Ar), 7.0 (s, 1H, ArH) m.w. 671.14; m.s. +671.7

3-amino-5-{4-(4-piperazinyl-6,7-dimethoxy-2-quinazolinyl)-1-piperazinyl}-N-(aminoiminomethyl-6-chloro-2-pyrazinecarboxamide.2HCL (54). A solution of 3-amino -5-{4-(4-t-boc-piperazinyl-6,7-dimethoxy-2-quinazolinyl)-1-piperazinyl}-N-(aminoiminomethyl-6-chloro-2-pyrazinecarboxamide (53) (0.37 g, 0.5 mmol) in a solution of gaseous HCl/MeOH (1.9 g/200 mL) was stirred in a sealed flask at rm. temp. for 16 hrs. The solution was conc. in vacuo and triturated with ether to afford the product. See FIG. 1. NMR $^1$H 3.6–4.2 (m, 22H, piperazinyl, OCH$_3$), 7.2 (s, 2H, ArH) m.w. 571.0; m.s. +287.1.

Example 35

3-amino-5-{4-(4-piperazinyl-6,7-dimethoxy-2-quinazolinyl)-1-piperazinyl}-6-chloro-2-pyrazinecarboxlic acid, methyl ester (55)

3-amino-5-{4-(4-piperazinyl-6,7-dimethoxy-2-quinazolinyl)-1-piperazinyl}-6-chloro-2-pyrazinecarboxlic acid, methyl ester (55). A solution of 3-amino-5-{4-(4-t-boc-piperazinyl-6,7-dimethoxy-2-quinazolinyl)-1-piperazinyl}-6-chloro-2-pyrazinecarboxylic acid methyl ester (52) (0.2 g)

in gaseous HCl/MeOH (3.0 g/100 mL) was stirred in a sealed flask for 16 hrs. The solution was conc. in vacuo and triturated with ether to afford the product. See FIG. 1. $^1$H DMSO 3.5–4.2 (m, 22 h, piperazine, OCH$_3$), 7.2 (s, 2H, ArH) m.w. 543.99 m.s.+544.6

Example 36

3-amino-5-{4-(4-t-boc-piperazinyl-6,7-dimethoxy-2-quinazolinyl)-1-piperazinyl}-6-chloro-2-pyrazinecarboxylic acid, sodium salt (56)

3-amino-5-{4-(4-t-boc-piperazinyl-6,7-dimethoxy-2-quinazolinyl)-1-piperazinyl}-6-chloro-2-pyrazinecarboxylic acid, sodium salt (56). A solution of 3-amino-5-{4-(4-t-boc-piperazinyl-6,7-dimethoxy-2-quinazolinyl)-1-piperazinyl}-6-chloro-2-pyrazinecarboxylic acid, methyl ester (52) (0.27 g) in a mixture of H$_2$O (100 mL) and THF (150 mL) containing NaOH (1.6 g) was heated at reflux for 16 hrs. The THF layer was separated, dried and conc. in vacuo. NMR $^1$H DMSO 1.4 (s, 9h, t-boc), 3.31–3.9 (m, 22 H, OCH$_3$, piperazine), 6.89 (s, 2H, Ar) m.w. 652.12; m.s. –629.13

Example 37

3-amino-5-{4-(2-ethylenediamino-6,7-dimethoxy-2-quinazolinyl)-1-piperazinyl}- 6-chloro-2-pyrazinecarboxylic acid, methyl ester (58)

2-Chloro-4-(2-t-boc-ethylenenediamine-6,7-dimethoxy-quinazoline). The title compound was prepared according to the procedures in Example 33 using mono-t-boc ethylenediamine in place of t-boc-piperazine. H$^1$ NMR DMSO 1.40 (s, 9H, t-Boc), 3.1–3.6 (m, 4H, CH$_2$), 3.88 (s, 6H, OCH$_3$), 7.08 (s, 2H, ArH)

2-piperazinyl-4-(2-t-Boc-ethylenenediamino-6,7-dimethoxy-quinazoline). The title compound is prepared according to the procedures in Example 33. H$^1$ NMR DMSO 1.39 (s, 9H, t-Boc), 2.7 (bs, 4H, piperazinyl), 3.2–3.7 (m, 16 H, CH$_2$, piperazinyl), 3.80–3.84 (s, 6H, OCH$_3$), 6.73 (s, 1H, ArH), 7.31 (s, 1H, Ar) m.w. 432.5 m.s. +433.

3-amino-5-{4-(2-t-Boc ethylenediamino-6,7-dimethoxy-2-quinazolinyl)-1-piperazinyl}-6-chloro-2-pyrazinecarboxylic acid, methyl ester (57). The title compound was prepared according to the procedures in Example 33. $^1$H NMR DMSO 1.39 (s, 9H, t-Boc), 3.2–3.91 (m, 21H, CH$_2$, OCH$_3$, piperazinyl), 6.78 (s, 1H, ArH), 7.28 (s, 1H, ArH) m.w. 617.93 m.s. +618.6, 620.4

Figure 2:
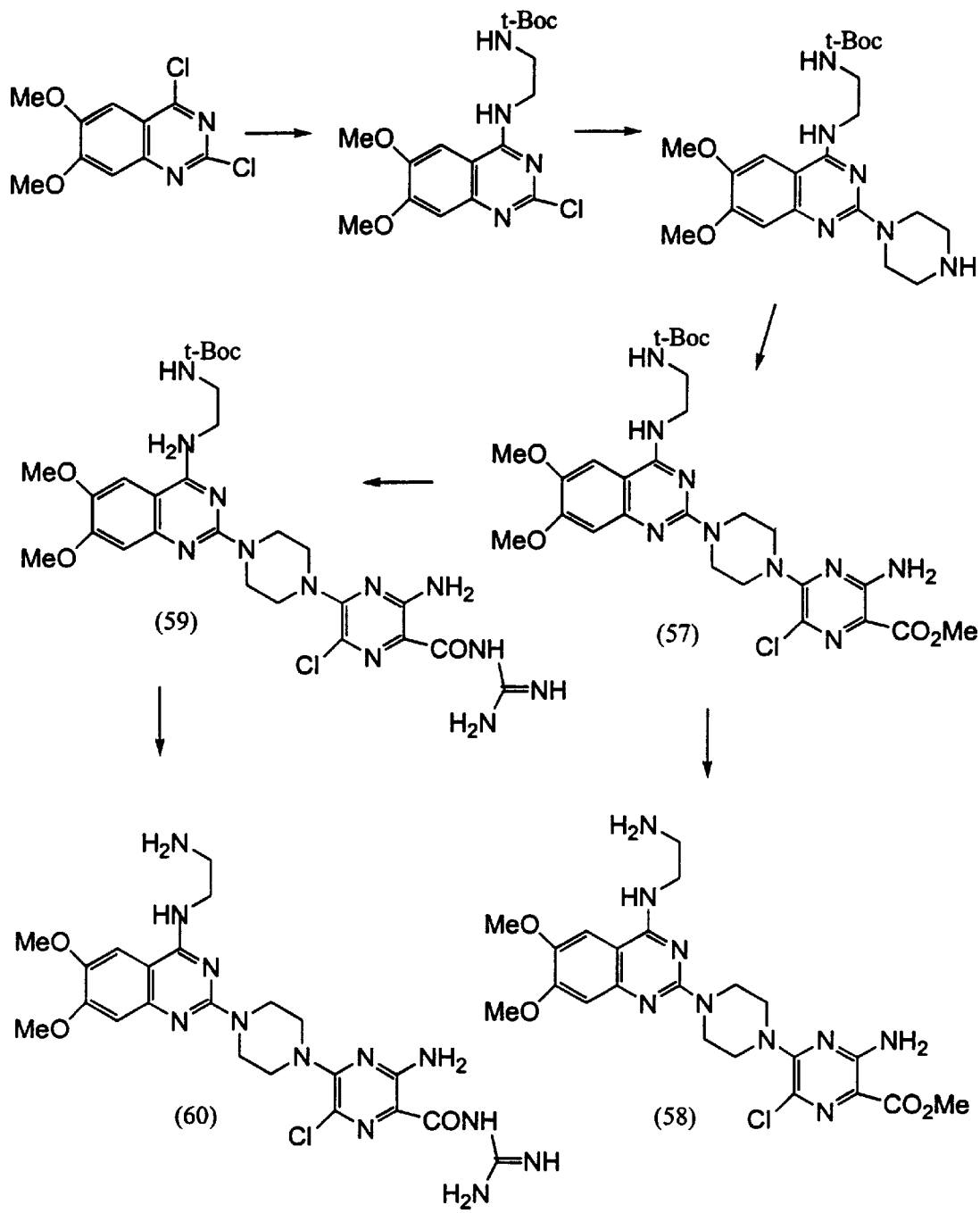
FIG. 2 is a schematic representation of a synthetic route for preparing compounds described in example 37.

3-amino-5-(4-(2-ethylenediamino-6,7-dimethoxy-2-quinazolinyl)-1-piperazinyl}-6-chloro-2-pyrazinecarboxylic acid ,methyl ester.HCl (58). The title compound was prepared from compound (57) according to the procedures in Example 34. See FIG. 2. $^1$H NMR DMSO 3.5–4.1 (m, 21H, CH$_2$, piperazinyl, OCH$_3$), 7.2 (s, 1H, ArH ), 7.66 (s, 1H, ArH) m.w. 517.89; m.s. +518.7

Example 38

3-amino-5-{4-(2-ethylenediamino-6,7-dimethoxy-2-quinazolinyl)-1-piperazinyl}-N-(aminoiminomethyl)-6-chloro-2-pyrazinecarboxamide (60)

3-amino-5-{4-(2-t-Boc ethylenediamino-6,7-dimethoxy-2-quinazolinyl)-1-piperazinyl}-N-6-(aminoiminomethyl)-6-chloro-2-pyrazinecarboxamide (59). The title compound was prepared from compound (57) according to the procedures in Example 33. $^1$H NMR DMSO 1.39 (s, 9H, t-Boc), 3.2–3.93 (m, 18H, CH$_2$ OCH$_3$, piperazinyl), 6.83 (s, 1H, ArH), 7.32 (s, 1H, ArH), m.w. 644.94; m.s. 645.7, 647.5

3-amino-5-{4-(2-ethylenediamino-6,7-dimethoxy-2-quinazolinyl)-1-piperazinyl}-N-(aminoiminomethyl)-6-chloro-2-pyrazinecarboxamide .2HCl (60). The title compound was prepared from compound (59) according to the procedures in Example 34. See FIG. 2. $^1$H NMR DMSO 3.5–4.16 (m, 20H, CH$_2$, piperazinyl, OCH$_3$), 7.35 (s, 1H, ArH), 7.77 (s, 1H, ArH) m.w. 544.98; m.s. +/2 273.7, 274.4

Example 39

2-{4-(piperazinyl-6,7-dimethoxy-2-quinazolinyl)-1-piperazinyl}-5-N-(aminoiminomethyl), pyridine (63)

2-piperazinyl-4-t-boc-piperazinyl-6,7-dimethoxy-quinazoline. A solution of 2-chloro-4-t-boc-piperazinyl-6,7-dimethoxy-quinazoline (10.1 g, 25 mmol, CH$_3$CN (500 mL), and piperazine (19 g, 220 mmol) was heated at reflux for 16 hrs. The ppt. was filtered off and conc. in vacuo and chromatographed on silica gel EtOAc/MeOH to afford the product. m.p. 127–130 $^1$H NMR DMSO 1.4 (s, 9H, t-boc), 2.92 (m, 4H, piperazinyl), 3.53 (m, 8H, piperazinyl), 3.87 (m, 10H, piperazinyl, OCH$_3$), 6.87 (s, 1H, Ar), 7.0 (s, 1H, Ar)

2-{4-(4-t-boc-piperazinyl-6,7-dimethoxy-2-quinazolinyl)-1-piperazinyl}-3-carboxylic acid, methyl ester-pyridine (61). The title compound was prepared according to the procedures in Example 33. $^1$H NMR DMSO 1.45 (s, 9H, t-Boc), 3.34 (s, 3H, CO$_2$Me), 3.3–3.92 (m, 22H, piperazinyl, OCH$_3$), 6.9 (s, 1h, ArH), 7.08 (s, 1H, ArH), 7.95 (d, 1H, het-H), 8.04 (d, 1H, het-H), 8.68 (d, 1H, het-H), m.w. 593.68; m.s. +594.7

2-{4-(4-t-boc-piperazinyl-6,7-dimethoxy-2-quinazolinyl)-1-piperazinyl}-5-N-(aminoiminomethyl)-pyridine (62). The title compound was prepared from compound (61) according to the procedures in Example 33. $^1$H NMR DMSO 1.46 (s, 9H, t-Boc), 3.2–3.9 (m, 22H, piperazinyl, OCH$_3$), 6.9 (s, 1H, ArH), 7.07 (s, 1H, ArH), 8.11 (d, 1H, het-H), 8.1.8 (d, 1H, het-H), 8.8 (d, 1H, het-H), m.w. 620.69 m.s. +621.3

Figure 3:
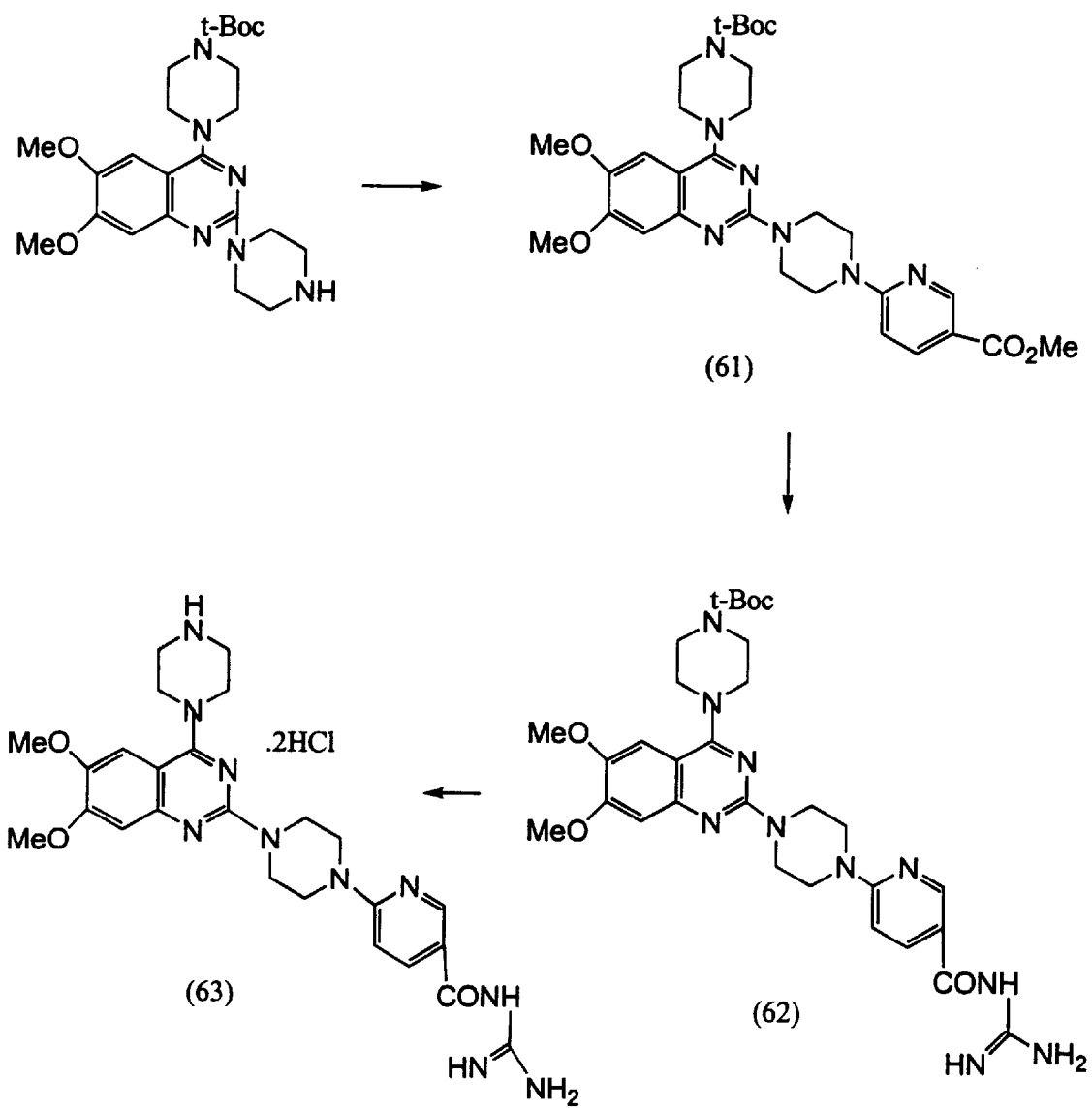
FIG. 3 is a schematic representation of a synthetic route for preparing compounds described in examples 38 and 39.

2-{4-(-piperazinyl-6,7-dimethoxy-2-quinazolinyl)-1-piperazinyl}-5-N-(aminoiminomethyl), pyridine.HCL (63). The title compound was prepared from compound (62) according to procedures in Example 34. See FIG. 3. $^1$H NMR DMSO 3.6–4.2 (m, 22H, piperazinyl, (OCH$_3$), 7.2 (s, 1H, ArH), 7.76 (s, 1H, ArH), 8.26 (d, 1H, het-H), 8.3 (d, 1H, het-H), 9.0 (d, 1H, het, H) m.w. 520.5; m.s. 521.8

Example 40

6,7-dimethoxy-2-(4-benzyloxy anilino)-4-quinazolamine (64)

6,7-dimethoxy-2-(4-benzyloxyanilino)-4-quinazolamine (64). 2-chloro-6,7-dimethoxy-4-quinazolinamine (1.73 g, 7 mmol) and 4-benzyloxyaniline (2.5 g, 12 mmol) were heated in an s.s. bomb at 145° C. for 16 hrs. Upon cooling the resultant solid was washed well with ether to afford the product. $^1$H NMR DMSO 3.86 (d, 6H , OCH$_3$), 5.14 (s, 2H, CH$_2$), 6.9–7.5 (m, 11H, ArH)

Example 41

In Vitro Antibacterial Activity

Bacterial Strains.

The *Streptococcus pyogenes* strains, *Klebsiella pneumoniae*, *Escherichia coli*, *Staphylococcus aureus*,

*Enterococcus faecalis* used in the antibacterial activity studies ATCC 14289, 49399, 13883, 25922, 13709, 29212, respectively, were obtained from the American Type Culture Collection, Rockville, Md. The strain *E. coli* imp- is a mutant strain of wild type *E. coli* with increased outer membrane permeability. In initial screens, *E. coli* imp- and *S. pyrogenes* (ATCC 14289) were used. The *E. coli* imp- strain was grown in LB broth, and the *S. pyogenes* strain was grown in Todd-Hewitt broth. Interesting compounds were further evaluated in the tier II screens against other bacterial screens. *S. aureus* was grown in trypticase soy broth, *E. faecalis* in Todd-Hewitt broth, wild type *E. coli* and *K. pneumoniae*, in nutrient broth. All bacterial were grown at 37° C.

Determination of Minimum Inhibitory Concentrations (MICs).

The assays were carried out in 150 μL volume in duplicate in 96-well clear flat-bottom plates. The bacterial suspension from an overnight culture growth in appropriate medium was added to a solution of test compound in 4% DMSO in water. Final bacterial inoculum was approximately $10^5$–$10^6$ CFU/well. The percent growth of the bacteria in test wells relative to that observed for a well containing no compound was determined by measuring absorbance at 595 nm ($A_{595}$) after 24 h. The MIC was determined as a range of single compound where the complete inhibition of growth was observed at the higher concentration and cells were viable at the lower concentrations. Both ampicillin and tetracycline were used as antibiotic-positive controls in each screening assay for *S. pyogenes, E. coli* imp-, *E. coli, S. aureus, E. faecalis, K. pneumoniae* and *P. vulgaris*. Ciprofloxacin was used as an antibiotic positive control in each screening assay for *P. aeruginosa*.

Animals and In Vivo Studies.

Male ICR mice were fed with autoclaved commercial food pellets and sterile water ad libitum. Mean weight at arrival was 20 g. Animals were inoculated intraperitoneally with $8.0 \times 10^6$ CFU/0.5 mL/mouse of *K. pneumoniae* (ATCC 10031) in BHI containing 5% mucin. Ten animals each were randomly assigned to either control or treatment groups. Compound (23) (DMSO solution, 100 mg/kg, 33.3 mg/kg and 3.3 mg/kg) and gentamycin (3 mg/kg, included as a positive control) were both administered subcutaneously one hour after infection. Compound (23) was administered as a solution in DMSO (100%) and 50 μL/mouse. Gentamycin was administered as an aqueous buffer solution (phosphate buffered saline (PBS), pH=7.4).

Coupled Bacterial Transcription/Translation Assay.

The DNA template, pBestLuc™ (Promega), is a plasmid containing a reporter gene for firefly luciferase fused to a strong tac promoter and ribosome binding site. Messenger RNA from 1 μg pBestLuc was transcribed and translated in *E. coli* S30 bacterial extract in the presence or absence of test compound. Compounds were tested in a black 96 well microtiter plate with an assay volume of 35 μL. Each test well contained: 5 μL test compound, 13 μL S30 premix (Promega), 4 μL 10× complete amino acid mix (1 mM each), 5 μL *E.coli* S30 extract and 8 μL of 0.125 μg/μL pBestLuc™. The transcription/translation reaction was incubated for 35 minutes at 37° C. followed by detection of functional luciferase with the addition of 30 μL LucLite™ (Packard). Light output was quantitated on a Packard TopCount.

Amino Acid Misincorporation Assay.

A mutant form of ubiquitin devoid of the amino acid tyrosine was produced in vitro in *E.coli* S-30 extracts in the presence of a tritiated tyrosine. Since ubiquitin has no tyrosine in the sequence, if tyrosine was used as the labeled amino acid, any incorporated counts above background were assumed to be due to the misincorporation of the tritiated amino acid. The labeled protein was captured via an ubiquitin antibody which was associated with anti-rabbit SPA beads. Altered ubiquitin molecules were not efficiently captured by the antibody. Compounds were tested in 96 well microtiter plate in an assay volume of 10 μL. Control experiments using the antibiotics, kanamycin, novabiocin, monensin, gentamicin, neomycin, tetracycline were run at 5 μM of each antibiotics. Compounds (2) and (28) were both tested at 5 μM, 50 μM, and 500 μM.

TABLE 1

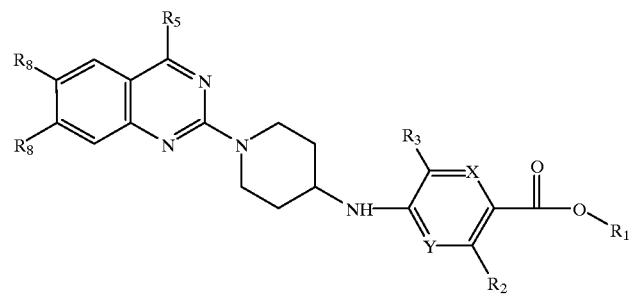

| Comp # | X | Y | $R_1$ | $R_2$ | $R_3$ | $R_5$ | $R_8$ $R_9$ | S. pyogenes (μM) | E. coli imp (μM) |
|---|---|---|---|---|---|---|---|---|---|
| 1 | N | N | Me | $NH_2$ | Cl | $NH_2$ | OMe | 12–25 | >25 |
| 2 | N | N | Me | $NH_2$ | H | $NH_2$ | OMe | >50 | >50 |
| 3 | C | N | Me | H | H | $NH_2$ | OMe | 25–50 | >50 |
| 4 | C | C | Me | H | H | $NH_2$ | OMe | 5–25 | 5–25 |
| 5 | C | C | tBu | H | H | $NH_2$ | OMe | 3–6 | 6–12 |
| 6 | C | C | tBu | H | N02 | $NH_2$ | OMe | 50–100 | 25–50 |
| 13 | C | C | tBu | H | H | H | OMe | >20 | >20 |
| 14 | C | C | tBu | H | H | OMe | OMe | <100[a] | <100[a] |
| 15 | C | C | tBu | H | H | OH | OMe | >100 | >100 |
| 16 | C | C | tBu | H | H | 4-mpa[b] | OMe | 2.5–5 | 10–20 |

TABLE 1-continued

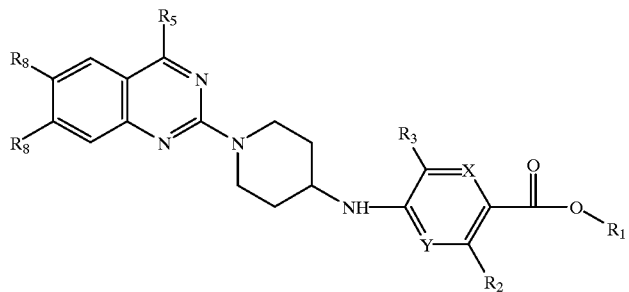

| Comp # | X | Y | $R_1$ | $R_2$ | $R_3$ | $R_5$ | $R_8$ $R_9$ | S. pyogenes ($\mu$M) | E. coli imp ($\mu$M) |
|---|---|---|---|---|---|---|---|---|---|
| 17 | C | C | tBu | H | H | $NH_2$ | H | <100[a] | <100[a] |
| 18 | N | N | H | $NH_2$ | Cl | $NH_2$ | OMe | >100 | >100 |
| 19 | N | N | H | $NH_2$ | H | $NH_2$ | OMe | >25 | >25 |
| 20 | C | N | H | H | H | $NH_2$ | OMe | >20 | >50 |
| 21 | C | C | H | H | $NO_2$ | $NH_2$ | OMe | >20 | >20 |
| 22 | C | C | H | H | H | $NH_2$ | OMe | >25 | 0.4–2 |
| 28 | C | C | H | H | H | H | OMe | >20 | >20 |
| 29 | C | C | H | H | H | OMe | OMe | >20 | >20 |
| 30 | C | C | H | H | H | OH | OMe | >20 | >20 |
| 31 | C | C | H | H | H | 4-mpa[b] | OMe | >20 | >20 |
| 32 | C | C | H | H | H | $NH_2$ | H | >100 | >100 |

[a]approximately 90% inhibition at 100 $\mu$M.
[b]4-mpa is —NH-(4-MePh)

TABLE 2

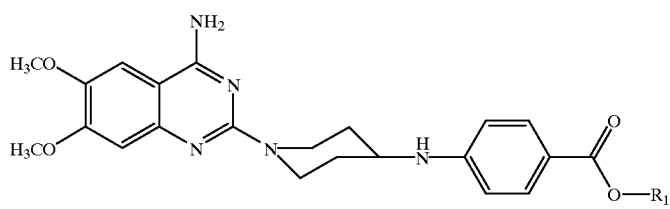

| Compd # | $R_1$ | K. pneumoniae (#13883) ($\mu$M) | E. coli[a] (#25922) ($\mu$M) | S. pyogenes (#49399) ($\mu$M) | S. aureus (#13709) ($\mu$M) | E. faecalis (#29212) ($\mu$M) |
|---|---|---|---|---|---|---|
| 4 | Me | >100 | >100 | 5–25 | >100 | 20–40 |
| 5 | tBu | >100 | >100 | 6–12 | >100 | 6–12 |
| 22 | H | 6–12 | 60–80 | >25 | 6–12 | >100 |

[a]wild type

We claim:

1. A compound of the formula (I)

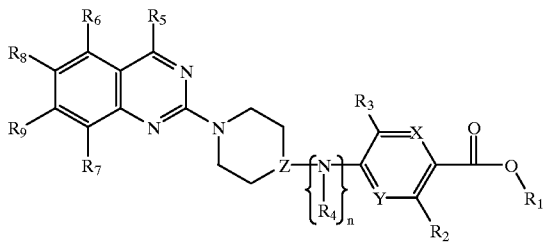

wherein
- X, Y and Z are independently CH or N;
- n is 0 or 1;
- $R_1$ is selected from OH, alkoxy, aryloxy, aralkoxy and guanidinyl;
- $R_2$ and $R_3$ are independently selected from H, halogen, amino, hydroxyl, nitro, cyano and carboxyl;
- $R_4$ is H, alkyl or acyl;
- $R_5$ is selected from H, hydroxyl, halogen, nitro, alkyl, alkoxy, amino, cyclic amino, alkylamino, arylamino and aralkylamino wherein the alkyl, aryl and cyclic moieties are optionally substituted;
- $R_6$ and $R_7$ are independently selected from H, alkyl, alkoxy, halogen and amino; and
- $R_8$ and $R_9$ are independently selected from H, alkyl, alkoxy, acyl, acyloxy, alkoxycarbonyl, hydroxyl, halogen, amino and carboxyl;
- provided that when $R_2$ and $R_5$ are both $NH_2$, $R_3$ is Cl, $R_6$ and $R_7$ are both H and $R_8$ and $R_9$ are both OMe, Z is N and n is 0 then $R_1$ is other than guanidinyl.

2. A compound according to claim 1, wherein n is 1 and Z is CH.

3. A compound according to claim 1, wherein $R_8$ and $R_9$ are both alkoxy.

4. A compound according to claim 3, wherein $R_8$ and $R_9$ are both methoxy.

5. A compound according to claim 1, wherein $R_5$ is $NH_2$ or NH-[4-Me-Ph].

6. A compound according to claim 1, wherein $R_6$ and $R_7$ are both H.

7. A compound according to claim 1, wherein $R_4$ is H.

8. A compound according to claim 1, wherein $R_1$ is OH.

9. A compound according to claim 1, wherein $R_1$ is $C_{1-4}$ alkoxy or guanidinyl.

10. A compound according to claim 9, wherein $R_1$ is methoxy.

11. A compound according to claim 9, wherein $R_1$ is t-butyloxy.

12. A compound according to claim 1, wherein X and Y are both CH.

13. A compound according to claim 12, wherein $R_1$ is OH, methoxy or t-butyloxy.

14. A compound according to claim 13, wherein $R_2$ and $R_3$ are both H.

15. A method of treating bacterial infection in a mammal comprising administering to said mammal an effective amount of a compound of formula (I)

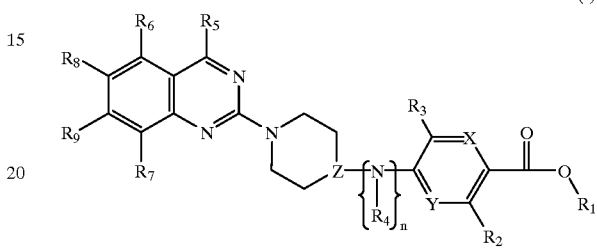

wherein
- X, Y and Z are independently CH or N;
- n is 0 or 1;
- $R_1$ is selected from OH, alkoxy, aryloxy, aralkoxy and guanidinyl;
- $R_2$ and $R_3$ are independently selected from H, halogen, amino, hydroxyl, nitro, cyano and carboxyl;
- $R_4$ is H, alkyl or acyl;
- $R_5$ is selected from H, hydroxyl, halogen, nitro, alkyl, alkoxy, amino, cyclic amino, alkylamino, arylamino and aralkylamino wherein the alkyl, aryl and cyclic moieties are optionally substituted;
- $R_6$ and $R_7$ are independently selected from H, alkyl, alkoxy, halogen and amino; and
- $R_8$ and $R_9$ are independently selected from H, alkyl, alkoxy, acyl, acyloxy, alkoxycarbonyl, hydroxyl, halogen, amino and carboxyl.

16. The method according to claim 15, wherein said mammal is a human.

17. The method according to claim 16, wherein said bacteria is *Streptococcus pyogenes, Enterococcus faecalis, Escherichia coli, Klebsiella pneumoniae* or *Staphylococcus aureus*.

* * * * *